(12) United States Patent
Ziegenbalg et al.

(10) Patent No.: US 10,792,910 B2
(45) Date of Patent: *Oct. 6, 2020

(54) MACHINE ARRANGEMENT AND METHOD FOR SEQUENTIAL PROCESSING OF SHEET-TYPE SUBSTRATES

(71) Applicant: KOENIG & BAUER AG, Würzburg (DE)

(72) Inventors: Christian Ziegenbalg, Weinböhla (DE); Uwe Becker, Radebeul (DE); Ulrich Köhler, Radebeul (DE); Frank Schumann, Moritzburg/Friedewald (DE); Carsten Reinsch, Radebeul (DE); Michael Koch, Dresden-Cossebaude (DE)

(73) Assignee: KOENIG & BAUER AG, Würzburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/716,741

(22) Filed: Dec. 17, 2019

(65) Prior Publication Data

US 2020/0122453 A1    Apr. 23, 2020

Related U.S. Application Data

(63) Continuation of application No. 16/034,580, filed on Jul. 13, 2018, now Pat. No. 10,556,422, which is a (Continued)

(30) Foreign Application Priority Data

Sep. 9, 2015  (DE) .................... 10 2015 217 229
Apr. 29, 2016 (WO) ................. PCT/EP2016/059647

(51) Int. Cl.
*B41F 19/00* (2006.01)
*B41F 23/04* (2006.01)
(Continued)

(52) U.S. Cl.
CPC ............. *B41F 19/001* (2013.01); *A61B 3/005* (2013.01); *A61B 3/0025* (2013.01); *A61B 3/04* (2013.01);
(Continued)

(58) Field of Classification Search
CPC .... B41F 19/001; B41F 19/007; B41F 19/008; B41F 21/05; B41F 23/0453;
(Continued)

(56) References Cited

U.S. PATENT DOCUMENTS 5,377,589 A    1/1995  Kruger
5,555,805 A *  9/1996  Lapp ................ B41F 13/02
                                                     101/228

(Continued)

FOREIGN PATENT DOCUMENTS

DE    243 007 A1    2/1987
DE    10047040 A1   4/2001
(Continued)

OTHER PUBLICATIONS

International Search Report of PCT/EP2016/069066 dated Feb. 28, 2017.

(Continued)

*Primary Examiner* — David H Banh
(74) *Attorney, Agent, or Firm* — Mattingly & Malur, PC

(57) ABSTRACT

A machine arrangement, that sequentially processes sheet-type substrates, includes a plurality of different processing stations, one of which includes a non-impact printing device that prints the substrates. Further processing stations are a primer application device that primes the substrates and a dryer for drying the primer applied to the substrates. The primer application device and the dryer precede the non-impact printing device, in the direction of travel of the substrates. The processing station including the non-impact
(Continued)

printing device, also includes a printing cylinder, on the circumference of which, the non-impact printing device that prints the substrates is arranged.

12 Claims, 15 Drawing Sheets

Related U.S. Application Data continuation of application No. 15/757,660, filed as application No. PCT/EP2016/069066 on Aug. 10, 2016, now Pat. No. 10,259,211.

(51) Int. Cl.

| | | |
|---|---|---|
| *B41J 3/54* | (2006.01) | |
| *B41J 3/60* | (2006.01) | |
| *B41J 11/00* | (2006.01) | |
| *B41F 25/00* | (2006.01) | |
| *B41F 21/05* | (2006.01) | |
| *A61B 3/00* | (2006.01) | |
| *A61B 3/04* | (2006.01) | |
| *A61B 3/103* | (2006.01) | |
| *A61B 3/14* | (2006.01) | |

(52) U.S. Cl.
CPC ............... *A61B 3/103* (2013.01); *A61B 3/14* (2013.01); *B41F 19/007* (2013.01); *B41F 19/008* (2013.01); *B41F 21/05* (2013.01); *B41F 23/0453* (2013.01); *B41F 23/0456* (2013.01); *B41F 23/0466* (2013.01); *B41F 25/00* (2013.01); *B41J 3/546* (2013.01); *B41J 3/60* (2013.01); *B41J 11/002* (2013.01); *B41J 11/0015* (2013.01); *B41P 2217/11* (2013.01)

(58) Field of Classification Search
CPC .. B41F 23/0456; B41F 23/0466; B41F 25/00; B41F 3/546; B41F 3/60; B41F 11/02
See application file for complete search history.

(56) References Cited

U.S. PATENT DOCUMENTS

| | | | |
|---|---|---|---|
| 5,927,195 A | 7/1999 | Volz | |
| 5,983,793 A | 11/1999 | Volz | |
| 6,708,612 B1 | 3/2004 | Schmidt | |
| 6,718,908 B1 | 4/2004 | Bayer | |
| 9,440,427 B2 | 9/2016 | Schmidt | |
| 2005/0150408 A1 | 7/2005 | Hesterman | |
| 2006/0208412 A1* | 9/2006 | Reinhard | B41F 11/02 |
| | | | 271/10.01 |
| 2008/0236421 A1* | 10/2008 | Ito | B41F 31/00 |
| | | | 101/217 |
| 2009/0079784 A1 | 3/2009 | Chiwata | |
| 2009/0231407 A1 | 9/2009 | Kachi | |
| 2009/0241787 A1 | 10/2009 | DiGenova | |
| 2009/0244237 A1 | 10/2009 | Kachi | |
| 2009/0291215 A1 | 11/2009 | Makuta | |
| 2009/0311426 A1* | 12/2009 | Nakazawa | B41J 2/2114 |
| | | | 427/256 |
| 2012/0128395 A1 | 5/2012 | Izawa | |
| 2012/0314013 A1 | 12/2012 | Takemoto et al. | |
| 2013/0021402 A1 | 1/2013 | Tsuzawa | |
| 2013/0222500 A1 | 8/2013 | Chiwata | |
| 2014/0331877 A1 | 11/2014 | Kamoda | |

FOREIGN PATENT DOCUMENTS

| | | |
|---|---|---|
| DE | 10312870 A1 | 2/2004 |
| DE | 102004002132 A1 | 8/2005 |
| DE | 102005021185 A1 | 11/2005 |
| DE | 102005021186 A1 | 11/2005 |
| DE | 102009000513 A1 | 8/2010 |
| DE | 102009000518 A1 | 8/2010 |
| DE | 102009000521 A1 | 8/2010 |
| DE | 102012200650 A1 | 8/2012 |
| DE | 102012218840 A1 | 5/2013 |
| DE | 102013209908 A1 | 12/2013 |
| DE | 102013215277 A1 | 3/2014 |
| DE | 102013019814 A1 | 6/2014 |
| DE | 102013211250 A1 | 12/2014 |
| DE | 102014010904 B3 | 1/2015 |
| EP | 0 620 115 A1 | 10/1994 |
| EP | 1 818 177 A2 | 8/2007 |
| EP | 1839903 A2 | 10/2007 |
| EP | 2540513 A1 | 1/2013 |
| GB | 2511606 A | 9/2014 |
| JP | H02-070438 A | 3/1990 |
| JP | 3-47123 U | 5/1991 |
| JP | 2004-034641 A | 2/2004 |
| JP | 2009-160934 A | 7/2009 |
| JP | 2012-076334 A | 4/2012 |
| JP | 2012-179737 A | 9/2012 |
| JP | 2014-210438 A | 11/2014 |
| JP | 2015-044345 A | 3/2015 |
| JP | 2015-047819 A | 3/2015 |
| JP | 2015-063398 A | 4/2015 |
| WO | 2004/013704 A1 | 2/2004 |
| WO | 2006/043269 A2 | 4/2006 |
| WO | 2010/086203 A1 | 8/2010 |
| WO | 2010/086205 A1 | 8/2010 |
| WO | 2013/178675 A1 | 12/2013 |

OTHER PUBLICATIONS

Jul. 22, 2019 Office Action issued in Japanese Patent Application No. 2018-512561.

* cited by examiner

MACHINE ARRANGEMENT AND METHOD FOR SEQUENTIAL PROCESSING OF SHEET-TYPE SUBSTRATES

CROSS-REFERENCE TO RELATED APPLICATIONS

This application is a continuation of prior U.S. patent application Ser. No. 16/034,580, filed Jul. 13, 2018, which is a continuation of prior U.S. patent application Ser. No. 15/757,660, filed Mar. 6, 2018, now U.S. Pat. No. 10,259,211, issued Apr. 16, 2019. That application is the U.S. National Phase, under 35 U.S.C. § 371, of PCT/EP2016/069066, filed Aug. 10, 2016; published as WO2017/041981 A1 on Mar. 16, 2017 and claiming priority to DE 10 2015 217 229.5, filed Sep. 9, 2015, and to PCT/EP2016/059647, filed Apr. 29, 2016.

FIELD OF THE INVENTION

The present invention relates to a machine arrangement having a plurality of different processing stations for the sequential processing of sheet-type substrates, and to a method for the sequential processing of sheet-type substrates. The machine comprises a plurality of different processing stations. One of these processing stations includes a non-impact printing unit for printing each of the substrates. A primer application unit, for priming each of the substrates, and a dryer, for drying the primer applied to the substrates in question, are provided as additional processing stations. The primer application unit and the dryer are each located upstream of the non-impact printing unit in a transport direction of the substrates in question. The processing station that comprises the non-impact printing unit includes a printing cylinder. The non-impact printing unit for printing each of the substrates is located on the periphery of the printing cylinder. The primer application unit is situated for applying the primer to the front side of each of the substrates and the dryer is situated for drying the front side of each of the primed substrates. In the method for the sequential processing of sheet-type substrates, in which the substrates are each processed one after the other on one of a front and a back side of the production line, a plurality of different processing stations are utilized. In each case, a printing ink or ink is applied to the respective side of each of the substrates in a processing station comprising at least one non-impact printing unit. Prior to the application of any printing ink or ink to the side in question of the substrates, an undercoating of an initial coating is first applied in a different processing station. Prior to the application of any printing ink or ink to the side in question of the substrates, the undercoating or initial coating is dried in a further processing station. The application of the undercoating or initial coating to the side in question of the substrates is carried out, in each case, in a processing station which is embodied as a primer application unit or in a processing station which is embodied as a cold foil application unit.

BACKGROUND OF THE INVENTION

WO 2004/013704 A1 describes a digital printing machine for direct non-contact sheet-fed printing having a digital printing couple that is unformatted in the circumferential direction, and having a transport apparatus downstream from the digital printing couple, wherein the transport apparatus has grippers for holding sheets on its periphery, the transport apparatus preferably having a plurality of transport cylinders and/or transport belts and/or impression cylinders.

EP 2 540 513 A1 describes a machine arrangement for the sequential processing of a plurality of sheet-type substrates, each having a front side and a back side, said machine arrangement comprising a first printing cylinder and a second printing cylinder, wherein at least one first non-impact printing unit, which prints the front side of the substrate in question, and a dryer, which dries the front side of the substrate in question that has been printed by the first non-impact printing unit, are arranged downstream from the first non-impact printing unit in the direction of rotation of the first printing cylinder, each on the periphery of the first printing cylinder, wherein at least one second non-impact printing unit, which prints the back side of the substrate in question, and a dryer, which dries the back side of the substrate in question that has been printed by the second non-impact printing unit, are arranged downstream from the second non-impact printing unit in the direction of rotation of the second printing cylinder, each on the periphery of the second printing cylinder, wherein the first printing cylinder and the second printing cylinder are arranged such that they form a common roller nip, wherein in this common roller nip, the first printing cylinder transfers the substrate in question, which has been printed on the front side and dried, directly to the second printing cylinder.

DE 103 12 870 A1 describes a digital printing machine for sheet-fed printing, having a digital printing couple that is format-free in the circumferential direction, an intermediate cylinder downstream from the digital printing couple, coated at least partially with an elastic material, and an impression cylinder downstream from the intermediate cylinder, wherein the impression cylinder has sheet-retaining grippers and the intermediate cylinder has recesses on its periphery for accommodating the grippers.

DE 10 2014 010 904 B3 describes an apparatus for two-sided printing of sheet-type printing stock, wherein the printing stock is guided around more than 360° on an impression cylinder, wherein the active region of an ink application unit, which has already printed the front side of the printing stock on an impression cylinder upstream, is re-entered by the printing stock, this time with its back side facing the ink application unit, wherein the ink application unit can preferably be pivoted between two impression cylinders disposed downstream from one another, and wherein the pivotable ink application unit is an inkjet print head, for example.

DE 10 2009 000 518 A1 describes a sheet-fed printing machine having a feed unit for loading printing sheets to be printed into the sheet-fed printing machine, and having at least one printing couple and/or coating unit for printing the printing sheets with a static print image that is identical for all printing sheets, and having a delivery unit for discharging printed sheets from the sheet-fed printing machine, and having at least one printing forme-free printing unit integrated into the sheet-fed printing machine for printing the printing sheet with a dynamic, variable print image in particular, wherein the/each printing forme-free printing unit is integrated into the sheet-fed printing machine, where it can be controlled as a function of the process parameters or operating parameters or order parameters or quality parameters.

A printing machine having a plurality of printing couples that print jointly onto a printing stock is known from DE 10 2013 211 250 A1, wherein at least two of these printing couples are arranged in a row, one behind the other, along a transport path provided for the printing stock, wherein at least one of these printing couples arranged in the row is embodied as an inkjet system, wherein the inkjet system in question is embodied such that this inkjet system prints information that varies or at least is variable during an ongoing printing process onto a target surface provided on the printing stock.

From DE 10 2005 021 185 A1, a device for applying opaque white or an effect color layer is known, wherein after the effect color layer is applied, it is dried or cured and then overprinted, wherein one or more inkjet print heads are provided within a printing machine, wherein the inkjet print head(s) for applying the opaque white layer or effect layer directly to the printing stock or indirectly to the printing stock via an intermediate carrier is/are located upstream of the infeed into or within the printing machine in the transport path of the printing stock.

EP 1 839 903 A2 discloses a method for transferring image-providing and/or covering or overlaying application layers from a transfer film to printing sheets in a sheet-processing machine, in particular a rotary sheet-processing machine, wherein the machine comprises at least one application mechanism for providing a printing sheet with an image-matching or full-surface adhesive coating, and at least one coating mechanism for transferring image-providing or covering layers from the transfer film to the printing sheets, wherein in a coating mechanism, a transfer nip is formed and the transfer film is placed on the surface of a pressing roller with the coated side on a printing sheet, and can be guided under pressure, together with said sheet, through the transfer nip, so that the image-providing or covering layers are transferred from the transfer film, adhering to the printing sheet in areas that are furnished with adhesive, wherein rigid-elastic printing sheets in the form of sheet metal panels or plastic panels are supplied to the printing machine, and are provided on at least one printed or coated, or one unprinted or uncoated first side in a transfer nip with an image-matching or full-surface foil coating from the transfer film, and wherein before and/or after application of the foil coating, the metal or plastic printing sheets are dried.

DE 10 2012 218 840 A1 discloses a method for transferring a detachable image-providing transfer layer from a transfer film to printing sheets that have been furnished with an adhesive coating by means of a coating mechanism, which contains an impression cylinder and a pressing roller that form a common transfer nip, through which the transfer film can be guided from a film supply roll, touching the pressing roller, such that the transfer film is guided, together with the printing sheet, through the transfer nip with the transfer layer resting on the printing sheet, which is guided on the impression cylinder, and under pressure for the purpose of transferring the coating, a) wherein adhesive is applied in the application unit to the printing sheet in a manner matching the image, b) wherein in the transfer nip, a subject on the transfer layer is transferred, under pressure, from the transfer film to the printing sheet that is provided with the adhesive image, c) wherein a protective layer is applied at least to the transfer layer applied in this way to the printing sheet, d) wherein after the protective layer is applied, the protective layer is dried on the printing sheet, and e) wherein once the protective layer has been dried, the printing sheet is overprinted with an image over a portion or all of its planar extension, including transfer layer and protective layer.

SUMMARY OF THE INVENTION

The object of the present invention is create a machine arrangement and a method, each for the sequential processing of a plurality of sheet-type substrates.

The object is achieved according to the invention by the provision of the non-impact printing unit being situated for printing the front side of each of the substrates. Three or four substrates are, or at least can be, arranged, one behind the other in each case, in the circumferential direction on the circumferential surface of each printing cylinder. A feed unit and a rocking gripper, that cooperates with a transfer drum, are provided. The substrates are picked up in the feed unit and are transferred individually, by use of the rocking gripper, to the transfer drum and from there are transferred to a rotating impression cylinder. The processing station that comprises the primary application unit for priming the front side of each of the substrates includes a printing couple cylinder, which cooperates with the impression cylinder and which has a forme roller in the form of an anilox roller which is, or at least can be, thrown onto this printing couple cylinder, and also includes at least one doctor blade that extends in the axial direction of the forme roller or an ink chamber blade system. The substrates that have been processed by one of the application of an undercoating or of an initial coating or by an application of printing ink or ink are dried using one of hot air and by irradiation with infrared radiation.

The advantages achieved with the invention will be clear from the following descriptions.

The approach described here can be used in a hybrid machine arrangement for processing sheet-type substrates, preferably in a hybrid printing machine that variably utilizes the high productivity of a conventional printing unit that prints, for example, by an offset printing method or by a flexographic printing method or by a screen printing method, or a coating unit, in particular a coating unit, in combination with at least one non-impact printing unit embodied as an inkjet printer, for example, that prints variable printed images in a flexible manner, wherein the conventional printing unit or coating unit and the non-impact printing unit are each used in an ongoing inline production process, each at its optimum working speed. Such a hybrid machine arrangement is very advantageous in particular for the production of packaging means, for example, sheets for the production of folding boxes, because the strengths of each one of the printing units can be utilized, resulting in a flexible and economical production of the packaging means. Transporting sheet-type substrates by means of rotating bodies, in particular cylinders and gripper bars or gripper carriages, each of which transfers the sheet-type substrates in a gripper closure to a next following processing station, as is known from sheet-fed offset printing machines, ensures the highest possible register accuracy.

BRIEF DESCRIPTION OF THE DRAWINGS

Exemplary embodiments of the invention are illustrated in the drawings and described in greater detail below.

DETAILED DESCRIPTION OF PREFERRED EMBODIMENTS

Figure 1:
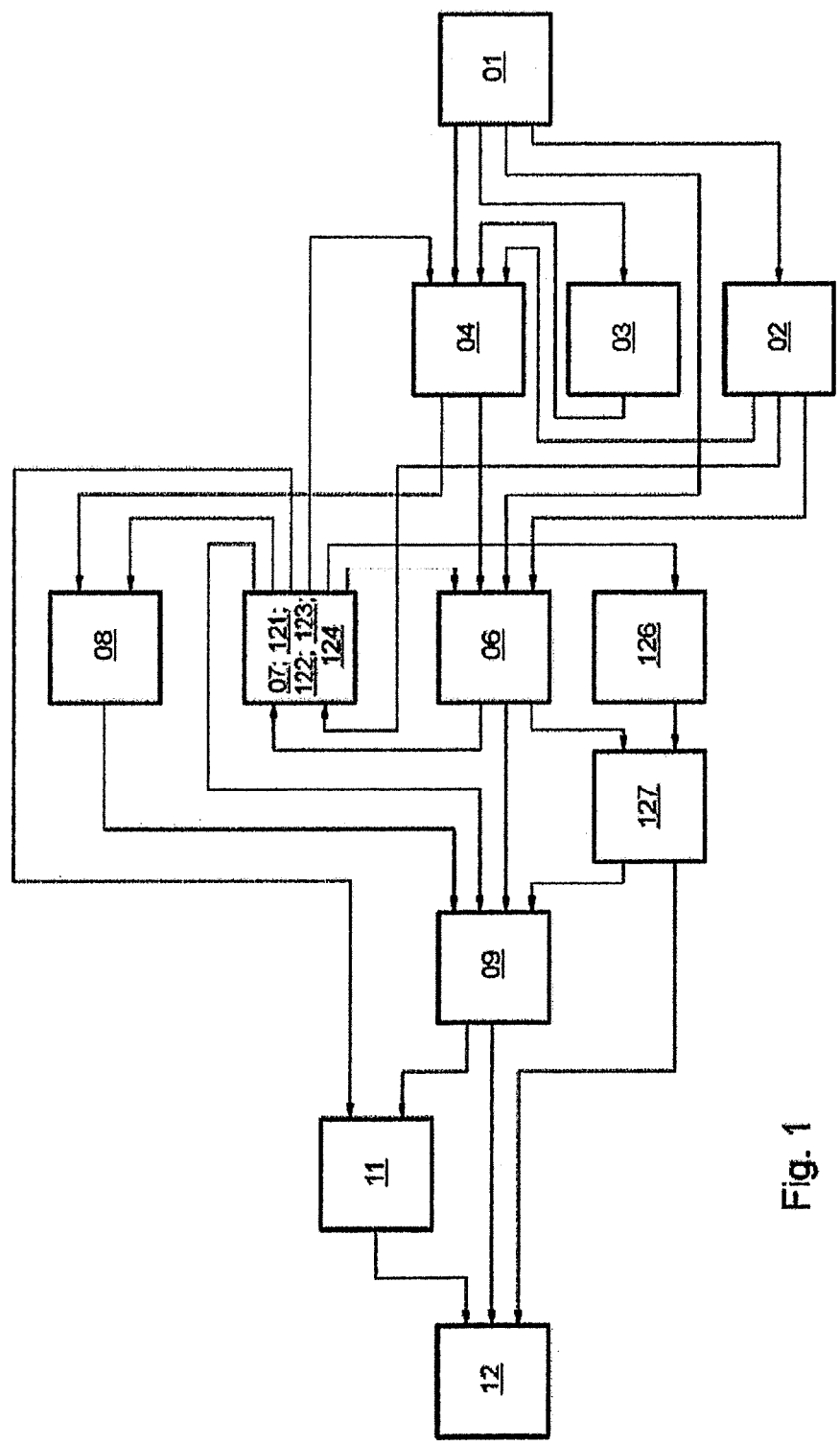
FIG. 1 shows a block diagram to illustrate the various production lines.

FIG. 1 is a block diagram illustrating various production lines, each being implementable with a machine arrangement having a plurality of different processing stations 01; 02; 03; 04; 06; 07; 08; 09; 11; 12, in particular, for processing at least one sheet-type substrate, in particular a printing stock, preferably a printing sheet, which is rectangular in particular, or more simply a sheet, wherein this at least one substrate is embodied as rigid or flexible, depending on the material, the thickness of the material and/or the base weight. Each of these processing stations 01; 02; 03; 04; 06; 07; 08; 09; 11; 12 is preferably embodied as an independently functional module, for example, wherein a module should be understood to be a machine unit or functional subassembly that is typically manufactured separately or at least is installed separately in its own frame. Each of processing stations 01; 02; 03; 04; 06; 07; 08; 09; 11; 12 disposed in the respective machine arrangement is thus preferably manufactured separately, and in a preferred embodiment can be tested individually in terms of its function, for example. Each machine arrangement, which is formed by selecting and assembling at least three different sheet processing stations 01; 02; 03; 04; 06; 07; 08; 09; 11; 12 that cooperate in a specific production process, embodies a specific production line. Each of the production lines shown, embodied as a certain machine arrangement having a plurality of processing stations 01; 02; 03; 04; 06; 07; 08; 09; 11; 12, is configured in particular for the production of a packaging means formed from the printing stock, preferably from the printed sheet. Each of the packaging means to be produced is, e.g. a folding box, which is produced from printed sheets. The various production lines are therefore configured in particular for producing different packaging means. The processing of the printing stock that is required during a specific production process is carried out inline, i.e., the processing stations 01; 02; 03; 04; 06; 07; 08; 09; 11; 12 that are involved in a specific production process are used one after another in an ordered sequence and in coordination with one another as the printing stock passes through the machine arrangement selected for said production process and comprising the respective processing stations 01; 02; 03; 04; 06; 07; 08; 09; 11; 12, without providing intermediate storage for the printing stock, i.e., the processed sheets, during the production process carried out by said machine arrangement.

All of the production lines shown in FIG. 1 have in common the fact that they each cooperate with a processing station 06 comprising at least one non-impact printing unit 06, preferably a plurality of non-impact printing units 06, for example, four, five, six or seven, each in particular individually controlled, wherein these non-impact printing units 06 are preferably arranged one behind the other in transport direction T of the printing stock and are embodied to be able to print the printing stock at least nearly over its entire width transversely to transport direction T. A non-impact printing unit 06 uses a printing method without a fixed printing forme and can in principle print the printing stock, e.g. a sheet that has just been supplied to said printing unit 06, with a print image that is different from the print image that preceded it, from one printing to the next. Each non-impact printing unit 06 is implemented in particular as at least one inkjet printer or as at least one laser printer. Inkjet printers are matrix printers, in which a print image is created by the targeted ejection or deflection of small ink droplets, such that the inkjet printer is embodied either as a device with a continuous ink jet (continuous ink jet=CIJ) or as a device that sprays individual ink droplets (drop on demand=DOD). Laser printers produce print images by an electrophotography method. Non-impact printing unit 06 is also referred to as a digital printing machine, for example.

In the following discussion, it is assumed by way of example that a sequence of flexurally rigid sheets, in particular, e.g. of a paper, a single-layer or multilayer paperboard or a cardboard, are processed in the respective machine arrangement by a plurality of processing stations 01; 02; 03; 04; 06; 07; 08; 09; 11; 12, in particular to produce a packaging means. Paper, paperboard and cardboard as printing stock differ in their respective base weight, i.e., the weight in grams for a square meter of this printing stock. In general, the aforementioned printing stock having a base weight between 7 $g/m^2$ and 150 $g/m^2$ is classified as paper, between 150 $g/m^2$ and 600 $g/m^2$ is paperboard and more than 600 $g/m^2$ is cardboard. Paperboard, which has good printability and is suitable for a subsequent finishing or processing such as coating and punching, is used in particular to produce folding boxes. In terms of pulp content, these types of cardboard may be, for example, wood-free, may have a low wood content or some wood content, or may contain recycled paper. In terms of construction, multilayer paperboards have a cover layer, an insert and a substrate as a back side. In terms of surface properties, paperboards may be uncoated, pigmented, coated or cast-coated, for example. The sheet format may range from 340 mm×480 mm to 740 mm×1060 mm, for example, with the first number in the format specification typically indicating the length in transport direction T of the sheets, and the second number representing the width of the sheet orthogonally to transport direction T.

In the block diagram in FIG. 1, each production line that can be represented with a plurality of processing stations 01; 02; 03; 04; 06; 07; 08; 09; 11; 12 runs substantially from right to left, with each of the directional arrows that connect two processing stations 01; 02; 03; 04; 06; 07; 08; 09; 11; 12 to one another indicating a transport path to be traveled by the printing stock and the associated transport direction T for traveling from one processing station 01; 02; 03; 04; 06; 07; 08; 09; 11; 12 to the next processing station 01; 02; 03; 04; 06; 07; 08; 09; 11; 12 selected in the machine arrangement intended for the respective production process. Each production process begins with sheets being provided in processing station 01, with processing station 01 being embodied as a feed unit 01, e.g. as a sheet feed unit 01 or as a magazine feed unit 01. A sheet feed unit 01 typically receives a pile of sheets stacked on a pallet, for example, whereas a magazine feed unit 01 comprises a plurality of compartments, into each of which sheets, in particular piles of different types of sheets or sheets of different formats, are or at least can be inserted. Feed unit 01 separates the stacked sheets for single feed, for example, by means of a suction head 41, and guides them in a sequence of separated sheets or in a shingled stream to the next processing station 02; 03; 04; 06 in the specific production process. The next processing station 02; 03; 04 is embodied, for example, as a primer application unit 02 or as a cold foil application unit 03 or as an offset printing unit 04 or as a flexographic printing unit 04. The next processing station 06 may also be, e.g. the at least one non-impact printing unit 06 directly. Offset printing unit 04 is preferably embodied as a sheet-fed offset printing machine, in particular as a sheet-fed printing machine having a plurality of printing couples 86 arranged based on the unit construction principle. Offset printing unit 04 provides the sheets with at least one static print image, i.e., a print image that does not vary during the printing process because it is bound to the printing forme used, whereas non-impact printing unit 06 provides the sheets with at least one print image that varies or is at least variable.

If the processing station 03 immediately following feed unit 01 is the cold foil application unit 03, then the sheet is typically transported from there to processing station 04, embodied as offset printing unit 04. In coil foil application unit 03, a metallized coating layer that is released from a carrier film is transferred to the printing stock. A wide variety of different metal effects can be achieved by overprinting this coating layer with an offset printing unit 04, for example. Cold foil application unit 03 is advantageously embodied as integrated into offset printing unit 04, for example, in that two additional printing couples 87; 88 are provided in offset printing unit 04. A special adhesive is applied to the printing stock, i.e., the sheet, by means of a standard printing forme in the first printing couple 87 in transport direction T of the printing stock. A second printing couple 88 in transport direction T of the printing stock is furnished with a film transfer device having the coating layer to be transferred. The film that carries the coating layer is guided from an unwinding station to a press nip between a transfer cylinder and a printing cylinder that cooperates with this transfer cylinder, and is thereby brought into contact with the printing stock. An aluminum layer and a protective coating layer, the coloring of which influences the color effect, provide coloring in the coating layer. By adhesion of an adhesive layer to the glue layer printed thereon, the transfer layers are left adhering to the substrate. The backing film is then wound up again. After the cold foil transfer, overprinting using conventional printing inks and UV inks and hybrid inks is possible inline, in particular in offset printing unit 04, in order to produce a variety of metallic color shades.

A printing stock, which is particularly absorbent, for example, and/or is to be prepared for printing in a non-impact printing unit 06, is supplied by feed unit 01 to the next processing station 02, embodied, for example, as a primer application unit 02 for coating at least one surface of the printing stock with a water-based primer, for example, in particular to seal the surface prior to printing or coating. Priming involves an undercoating or initial coating of the printing stock to improve or enable adhesion of an ink or printing ink to be applied thereafter to the printing stock. Primer application unit 02 is formed, for example, in combination with a printing couple 86 of a rotary printing machine and comprises, for example, a printing couple cylinder 82 that cooperates with an impression cylinder 119 and includes a forme roller 83, preferably in the form of an anilox roller 83, which is or at least can be thrown onto this printing couple cylinder 82, as well as at least one doctor blade 84, in particular an ink chamber blade system 84 extending in the axial direction of the forme roller 83 (FIGS. 3 through 5, 8, 9). The primer is applied to the printing stock either over its full surface area or to only certain, i.e., previously defined, areas, i.e. partially, by means of primer application unit 02. The printing stock, e.g. sheets, processed in primer application unit 02, is fed, for example, to an offset printing unit 04 and/or a non-impact printing unit 06 as the next processing station.

The flexographic printing carried out by a processing station 04, embodied, e.g. as a flexographic printing unit 04, is a direct letterpress method, in which the raised areas of the printing forme are image-carrying areas, and which is frequently used for printing packaging materials made of paper, paperboard or cardboard, metallized film, or a plastic such as PE, PET, PVC, PS, PP, PC. In flexographic printing, low-viscosity printing inks and flexible printing plates made of photopolymer or rubber are used. In general, a flexographic printing unit 04 includes a) an anilox roller, by means of which the printing forme is inked, b) a printing cylinder, also known as a forme cylinder, to which the printing forme is attached, and c) an impression cylinder, which guides the printing stock.

Processing station 04, which is embodied as flexographic printing unit 04 or as offset printing unit 04 and prints each of the sheets with at least one static print image, preferably has a plurality of printing couples 86, e.g. at least four, wherein each printing couple 86 preferably prints with a different printing ink, so that the printing stock is printed in multiple colors, for example, in four-color printing, as it passes through flexographic printing unit 04 or offset printing unit 04. The color shades yellow, magenta, cyan and black in particular are used as the printing inks. In an alternative embodiment of printing unit 04 to the flexographic printing method or the offset printing method, the processing station 04 that prints the sheets with at least one static print image each is embodied as a printing unit 04 that prints by a screen printing method.

After the printing stock has been processed in at least one non-impact printing unit 06, this printing stock is sent to a processing station 07 embodied, for example, as an intermediate dryer 07, wherein this intermediate dryer 07 is embodied as a dryer that dries the printing stock in question by irradiation with infrared or ultraviolet radiation, with the type of radiation being dependent in particular on whether the ink or printing ink applied to the printing stock is water-based or UV curing. After intermediate drying, the printing stock is sent to a processing station 08 embodied as a coating unit 08, for example. Coating unit 08 applies a dispersion coating, for example, to the printing stock, dispersion coatings consisting essentially of water and binders (resins), with surfactants stabilizing these dispersions. A coating unit 08 that applies a dispersion coating to the printing stock consists either of an anilox roller, an ink chamber blade and a forme roller (comparable to a flexographic printing couple), or of a dipping roller and forme roller. Flat and/or partial coatings are applied by means of a printing forme, preferably based on photopolymerization, for example. Special coating plates made of rubber may also be used for full-surface coatings. Downstream of coating unit 08, a processing station 09 embodied, e.g. as a dryer 09 is arranged in the transport path of the printing stock, wherein this dryer 09 is embodied as a dryer that dries the printing stock in question by irradiation with infrared radiation or by hot air. If the machine arrangement in question has multiple dryers 07; 09 along the transport path of the printing stock, then the dryer with reference numeral 09 is preferably the last of these multiple dryers 07; 09 in transport direction T of the printing stock, wherein intermediate dryer(s) 07 and (final) dryer 09 are embodied identically or may also be embodied differently. If a printing stock that dries by ultraviolet radiation will be supplied to dryer 09, i.e., a printing stock on which an ink or printing ink that cures by UV radiation or a coating that cures by UV radiation, for example, a glossy coating, is applied, then this dryer 09 is equipped with a radiation source that generates ultraviolet radiation. More intense glossy effects and matte effects can be achieved with dispersion coatings as compared with the traditional oil printing coating. Special visual effects can be achieved with effect pigments in the coating. Primer application unit 02, cold foil application unit 03 and coating unit 08 can be combined under the umbrella term of coating unit 02; 03; 08.

After drying, the printing stock is sent to a processing station 11, for example, which carries out a mechanical further processing of the printing stock, for example, by punching, creasing and/or cutting parts, in particular separating copies from their attachment in the preferably printed sheet. Each of the aforementioned types of further processing is carried out in and/or by a processing unit 46. Mechanical further processing is preferably carried out in cooperation with a cylinder transporting the respective sheet. Afterward or directly from dryer 09, the printing stock is transferred to a delivery 12, which forms the last processing station 12 in each of the production lines formed by a specific arrangement of processing stations 01; 02; 03; 04; 06; 07; 08; 09; 11; 12, as illustrated in FIG. 1. The previously processed sheets are preferably stacked on a pallet, for example, in delivery 12.

As illustrated in FIGS. 2 through 8, the aforementioned sequence of processing stations 01; 02; 03; 04; 06; 07; 08; 09; 11; 12 included in the machine arrangement may be modified only by way of example and dependent upon the printed product to be produced in each case.

In the production lines illustrated in FIG. 1 by way of example and used in particular for the production of packaging means, each production line comprise a machine arrangement having a selection of the group of aforementioned processing stations 01; 02; 03; 04; 06; 07; 08; 09; 11; 12. The following production lines are or at least can be formed, for example:

1. Sheet feed unit 01; primer application unit 02; non-impact printing unit 06; intermediate dryer 07 with IR radiation source for dispersion coating; coating unit 08; dryer 09 with IR radiation source or hot air; delivery 12
2. Sheet feed unit 01; primer application unit 02; non-impact printing unit 06; dryer 09 with IR radiation source or hot air; delivery 12
3. Sheet feed unit 01; primer application unit 02; non-impact printing unit 06; intermediate dryer 07 with IR radiation source; coating unit 08 for dispersion coating and UV curing coating; dryer 09 with IR radiation source or hot air and with UV radiation source; delivery 12
4. Sheet feed unit 01; cold foil application unit 03; offset printing unit 04; non-impact printing unit 06; dryer 09 with IR radiation source or hot air; delivery 12
5. Sheet feed unit 01; primer application unit 02; non-impact printing unit 06; intermediate dryer 07 with IR radiation source for dispersion coating; coating unit 08; dryer 09 with IR radiation source or hot air; mechanical further processing unit 11; delivery 12
6. Sheet feed unit 01; offset printing unit 04; non-impact printing unit 06; intermediate dryer 07 with IR radiation source; mechanical further processing unit 11; delivery 12
7. Sheet feed unit 01; non-impact printing unit 06; dryer 09 with IR radiation source or hot air; delivery 12
8. Sheet feed unit 01; non-impact printing unit 06; intermediate dryer 07 with UV radiation source; dryer 09 with UV radiation source; delivery 12
9. Sheet feed unit 01; non-impact printing unit 06; intermediate dryer 07 with UV radiation source; dryer 09 with UV radiation source; mechanical further processing unit 11; delivery 12
10. Sheet feed unit 01; non-impact printing unit 06; intermediate dryer 07 with IR radiation source; offset printing unit 04; coating unit 08; dryer 09 with IR radiation source or hot air; delivery 12
11. Magazine feed unit 01; primer application unit 02; non-impact printing unit 06; intermediate dryer 07 with IR radiation source; coating unit 08; dryer 09 with IR radiation or hot air; delivery 12
12. Magazine feed unit 01; primer application unit 02; non-impact printing unit 06; intermediate dryer 07 with IR radiation source; dryer 09 with IR radiation source or hot air; mechanical further processing unit 11; delivery 12
13. Magazine feed unit 01; non-impact printing unit 06; intermediate dryer 07 with UV radiation source; coating unit 08; dryer 09 with UV radiation source; delivery 12

At least one of processing stations 01; 02; 03; 04; 07; 08; 09; 11; 12 that cooperates with the at least one non-impact printing unit 06 is selected to participate in the processing of sheets depending on whether the printing ink to be applied to the sheet by non-impact printing unit 06, in particular, is embodied as a water-based ink or printing ink or as a UV radiation-curing ink or printing ink. The machine arrangement is thus embodied for printing each of the sheets with a water-based printing ink or with a printing ink that cures by UV radiation.

Additional machine arrangements that will be explained in greater detail in reference to FIGS. 9 and 10 and that include a selection from the group of aforementioned processing stations 01; 02; 03; 04; 06; 07; 08; 09; 11; 12 provide production lines, for example, having essentially the following processing stations: sheet feed unit 01; first primer application unit 02; first dryer 121; first non-impact printing unit 06; second dryer 122; second primer application unit 126; third dryer 123; second non-impact printing unit 127; fourth dryer 124; delivery 12.

One advantageous machine arrangement mentioned as an example here has a plurality of processing stations for processing sheets, wherein a plurality of processing stations 01; 02; 03; 04; 06; 07; 08; 09; 11; 12 are arranged one behind the other in transport direction T of the sheets for inline processing of these sheets, wherein at least one of these processing stations 06 is embodied as a non-impact printing unit 06, wherein a first processing station 01 upstream of non-impact printing unit 06 in transport direction T of the sheets is embodied as a sheet feed unit 01 or as a magazine feed unit 01, wherein a processing station 08 located between first processing station 01 and non-impact printing unit 06 is embodied as a first coating unit 08, which applies a coating to each of the sheets, wherein a first dryer 07 is located between first coating unit 08 and non-impact printing unit 06, wherein a first transport cylinder assembly 17 is situated for transporting the sheets from first dryer 07 to non-impact printing unit 06, wherein a second dryer 07 is located downstream of non-impact printing unit 06 in transport direction T of the sheets, wherein a device for transferring the sheets coming from non-impact printing unit 06 to second coating unit 08 is provided, wherein a third dryer 09 is located downstream of second coating unit 08, and wherein a delivery 12 for the sheets is located downstream of the third dryer 09 in transport direction T of the sheets. In addition, a mechanical further processing unit 11 may be located between third dryer 09 and delivery 12. Further, a coating unit 03 that applies a cold foil, for example, is located upstream of non-impact printing unit 06 in transport direction T of the sheets. Non-impact printing unit 06 preferably has a plurality of individually controlled inkjet printers along the transport path of the sheets. In the active region of non-impact printing unit 06, the sheets are preferably guided such that they each rest flat on a transport apparatus, wherein the transport apparatus has a curved transport path for the sheets, at least in the active region of non-impact printing unit 06, the transport apparatus being embodied as a printing cylinder 22 in the active region of non-impact printing unit 06. Upstream of non-impact printing unit 06 in transport direction T of the sheets, a transfer device is provided, for example, wherein the transfer device aligns the sheets, for example, at least in their axial register and/or circumferential register, so that they maintain register accuracy relative to the printing position of non-impact printing unit 06, wherein the transfer device has a suction drum 32, for example, which holds each sheet by means of suction air. This machine arrangement is embodied to print each of the sheets, in particular, with a water-based printing ink or with a printing ink that cures under ultraviolet radiation. This machine arrangement is embodied in particular for producing various packaging means. The device for transferring the sheets coming from non-impact printing unit 06 to second coating unit 08 is embodied as a second transport cylinder assembly 19, for example.

Figure 2:
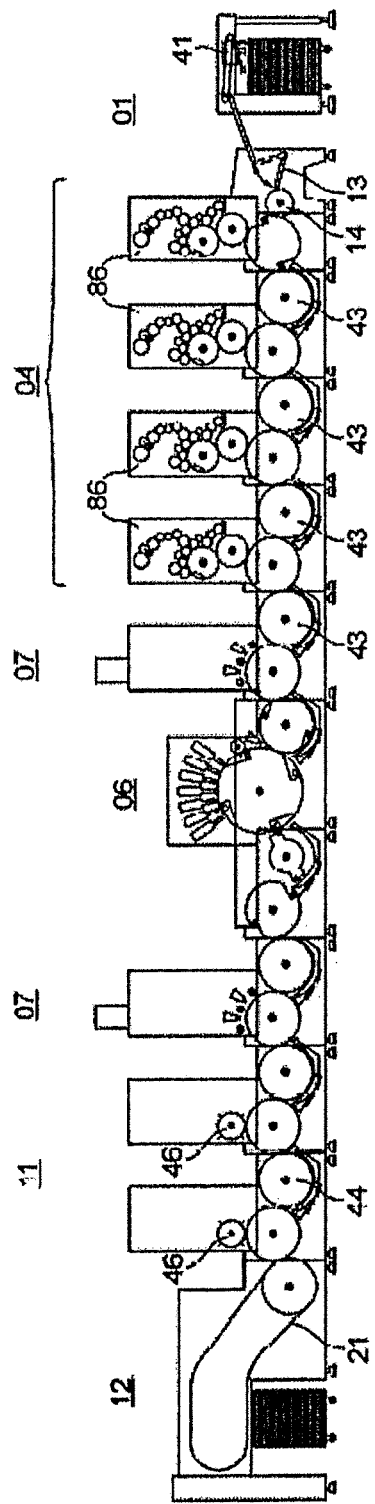
FIG. 2 shows a first machine arrangement having a plurality of different processing stations.

FIG. 2 shows as an example a machine arrangement having a plurality of processing stations 01; 02; 03; 04; 06; 07; 08; 09; 11; 12 according to production line No. 6 defined above. Sheets are gripped individually from a pile in a sheet feed unit 01 using a suction head 41, for example, and are transferred one after another in a cycle of 10,000 units per hour, for example, to an offset printing unit 04 having, for example, four printing couples 86 arranged in a row. For transferring the sheets from one printing couple 86 to the next arranged in a row, a rotating body, in particular a cylinder, preferably a transfer drum 43 is provided, each transfer drum being arranged between two immediately adjacent printing couples 86. Offset printing unit 04 receives the sheets supplied to it by sheet feed unit 01, for example, with a rocking gripper 13 and guides the sheets to a transfer drum 14 of offset printing unit 04, wherein the sheets are then guided from one printing couple 86 to the next in a gripper closure in offset printing unit 04. The sheets are printed on at least one side in offset printing unit 04. If a turning device 23 is present, the sheets can also be printed on both sides in offset printing unit 04, i.e., in perfecting printing. After passing through processing station 04, which is embodied here as an offset printing unit 04, for example, the sheet in question, preferably printed in four colors, is transferred by means of first transport cylinder assembly 17 to a non-impact printing unit 06. Non-impact printing unit 06 preferably comprises a plurality of inkjet printers, for example five, arranged in a linear row, in particular with each being controlled individually. The sheets that have been provided with at least one static print image in offset printing unit 04 and with at least one varying or at least variable print image in non-impact printing unit 06 are then dried in a dryer 07 or intermediate dryer 07, preferably with an IR radiation source. After that, the sheets are processed further in a mechanical further processing unit 11, for example, by punching and/or creasing and/or separating copies from the respective sheet. Lastly, the sheets and/or copies separated from the sheets are collected in a delivery 12, in particular being stacked. In the active region of first gripper system 16 and/or of the first chain conveyor 16, a delivery 12, in particular a multi-pile delivery, may be provided along the transport path provided for the sheets. A multi-pile delivery is likewise arranged, for example, downstream of mechanical further processing unit 11 in transport direction T of the sheets.

The sheets picked up from a pile in feed unit 01, in particular in sheet feed unit 01, are transported individually, spaced from one another, through offset printing unit 04 at a first transport speed. Sheets transferred from offset printing unit 04 to non-impact printing unit 06 are transported in said non-impact printing unit 06 at a second transport speed, wherein the second transport speed prevailing in non-impact printing unit 06 is typically lower than the first transport speed prevailing in offset printing unit 04. To adapt the first transport speed prevailing in offset printing unit 04 to the typically lower second transport speed prevailing in non-impact printing unit 06, for example, the sheet gap existing between immediately successive sheets, i.e., the distance resulting for the sheets transported in the gripper closure through offset printing unit 04 due to the gripper channel width, for example, is preferably reduced in the transfer of these sheets from offset printing unit 04 to non-impact printing unit 06, wherein such a reduction in distance ranges from 1% to 98%, based on the original distance, for example. Thus, directly successive sheets are also transported spaced a distance from one another in non-impact printing unit 06, but with a typically smaller sheet gap or at a shorter distance than in offset printing unit 04, and consequently, also at a lower second transport speed. This second transport speed is preferably maintained when sheets that have been printed in non-impact printing unit 06 are first transported to an intermediate dryer 07 or dryer 09, and from there, e.g. by means of a feed table, to a mechanical further processing unit 11 and on to delivery 12. However, the sheets may also be changed from their second transport speed to a third transport speed, for example, if required by mechanical further processing unit 11, wherein the third transport speed is typically higher than the second transport speed and corresponds, for example, to the first transport speed prevailing in offset printing unit 04, in particular. Upstream of mechanical further processing unit 11, for example, second transport cylinder assembly 19 is provided, which grips the sheets coming from intermediate dryer 07 or dryer 09 and transports them to mechanical further processing unit 11. In the area of mechanical further processing unit 11, which comprises a plurality of processing mechanisms 46 in a row, for example, a rotating body, in particular a cylinder, preferably a transfer drum 44, is provided for transferring the sheets from one processing mechanism 46 to the next in a row, each of these rotating bodies being arranged between two neighboring processing mechanisms 46. One of the processing mechanisms 46 is embodied, for example, as a punching mechanism, and another processing mechanism 46 is embodied, for example, as a creasing mechanism. The processing mechanisms 46 in question are embodied for carrying out the mechanical further processing of the sheets, preferably in cooperation with a cylinder transporting the respective sheet. After the sheets and/or the copies separated therefrom have undergone mechanical further processing, they are transported by means of a chain conveyor 21, for example, to delivery 12, where they are collected, preferably being stacked.

The sheets are transported from the outlet of offset printing unit 04 at least up to the outlet of intermediate dryer 07 or dryer 09, preferably to the intake of mechanical further processing unit 11, by means of a multipart transport apparatus, i.e. a transport apparatus consisting of a plurality of modules, in particular transport units, arranged one behind the other in transport direction T of the sheets, wherein the transport apparatus has a plurality of transport cylinders. An intermediate dryer 07 or a dryer 09 may also be disposed between offset printing unit 04 and non-impact printing unit 06 as needed.

FIGS. 3 through 8 schematically illustrate examples of additional machine arrangements, each comprising a plurality of processing stations 01; 02; 03; 04; 06; 07; 08; 09; 11; 12, wherein the reference numerals denote processing stations 01; 02; 03; 04; 06; 07; 08; 09; 11; 12 explained above as well as additional ones of their respective assemblies.

Figure 3:
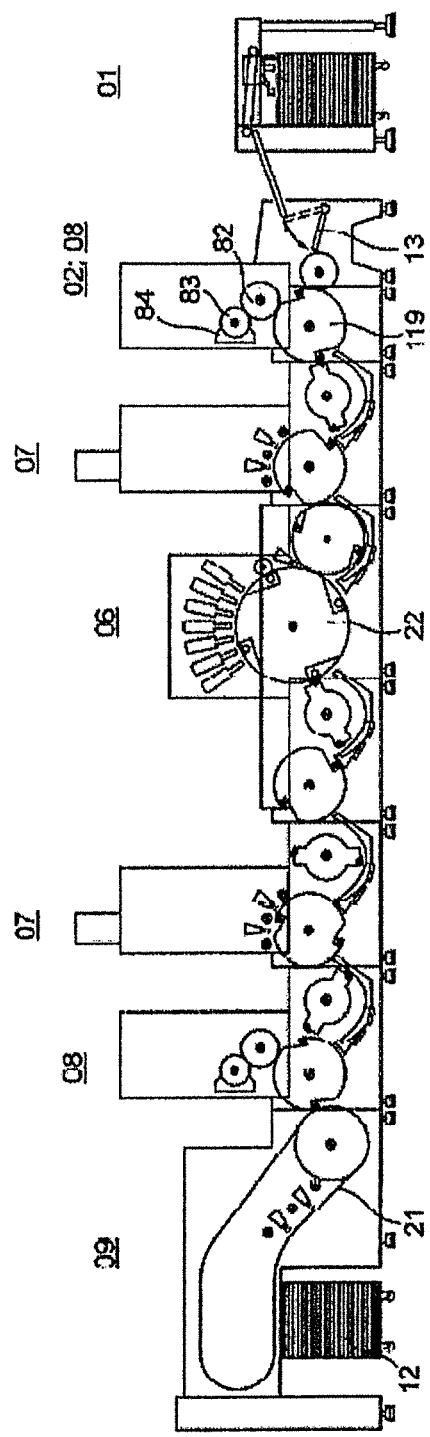
FIGS. 3 to 8 show additional machine arrangements, each having a plurality of different processing stations.

FIG. 3 shows a machine arrangement comprising the following processing stations 01; 02; 03; 04; 06; 07; 08; 09; 11; 12 arranged one behind the other in transport direction T of the printing stock: sheet feed unit 01; primer application unit 02 or coating unit 08; intermediate dryer 07; non-impact printing unit 06; intermediate dryer 07; coating unit 08; dryer 09; delivery 12.

Figure 4:
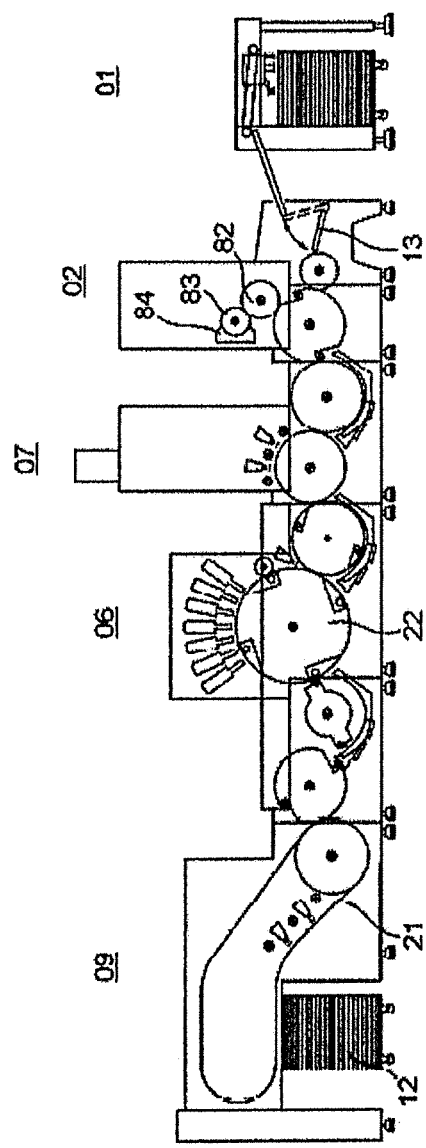

FIG. 4 shows a machine arrangement comprising the following processing stations 01; 02; 03; 04; 06; 07; 08; 09; 11; 12 arranged one behind the other in transport direction T of the printing stock: sheet feed unit 01; primer application unit 02; intermediate dryer 07; non-impact printing unit 06; dryer 09; delivery 12.

Figure 5:
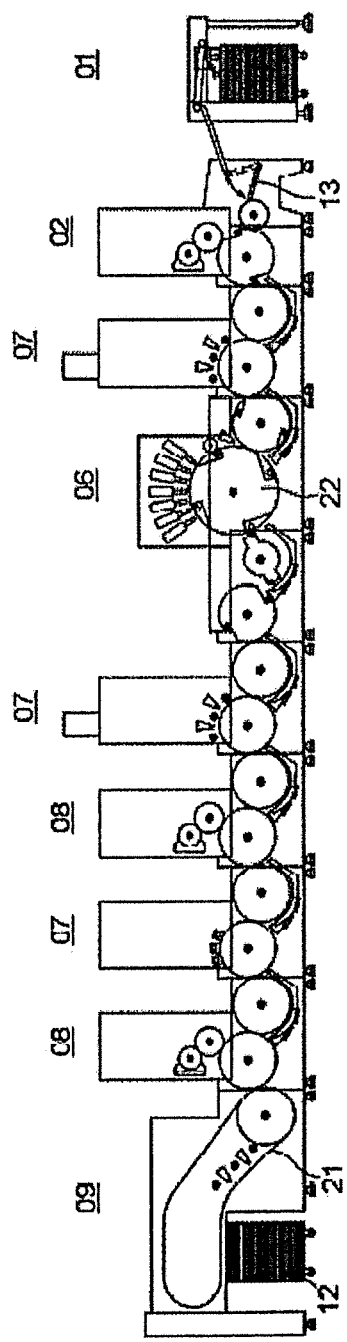

FIG. 5 shows a machine arrangement comprising the following processing stations 01; 02; 03; 04; 06; 07; 08; 09; 11; 12 arranged one behind the other in transport direction T of the printing stock: sheet feed unit 01; primer application unit 02; intermediate dryer 07; non-impact printing unit 06; intermediate dryer 07; coating unit 08; intermediate dryer 07; coating unit 08; dryer 09; delivery 12.

Figure 6:
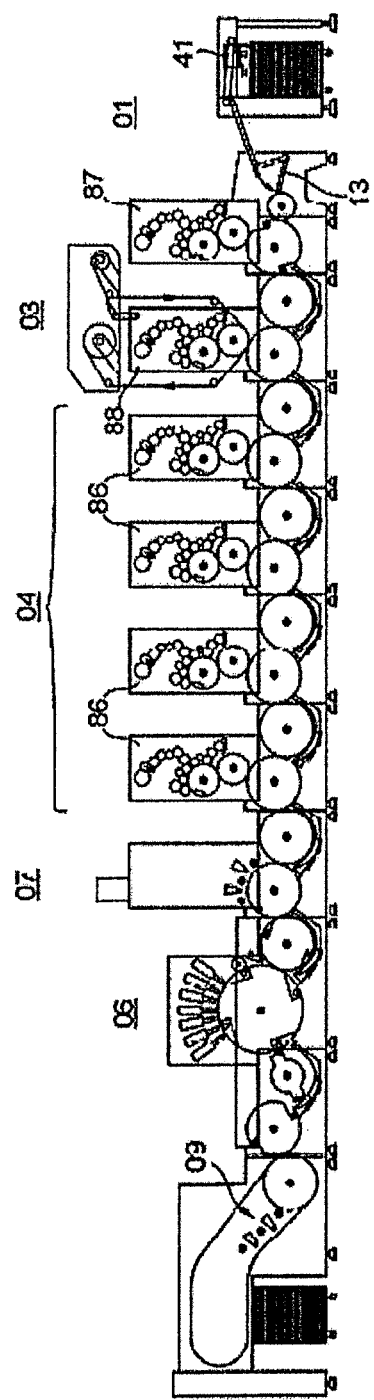

FIG. 6 shows a machine arrangement comprising the following processing stations 01; 02; 03; 04; 06; 07; 08; 09; 11; 12 arranged one behind the other in transport direction T of the printing stock: sheet feed unit 01; a first offset printing unit 04; cold foil application unit 03; four additional offset printing units 04 based on the unit construction principle; intermediate dryer 07; non-impact printing unit 06; intermediate dryer 07; non-impact printing unit 06; dryer 09; delivery 12.

Figure 7:
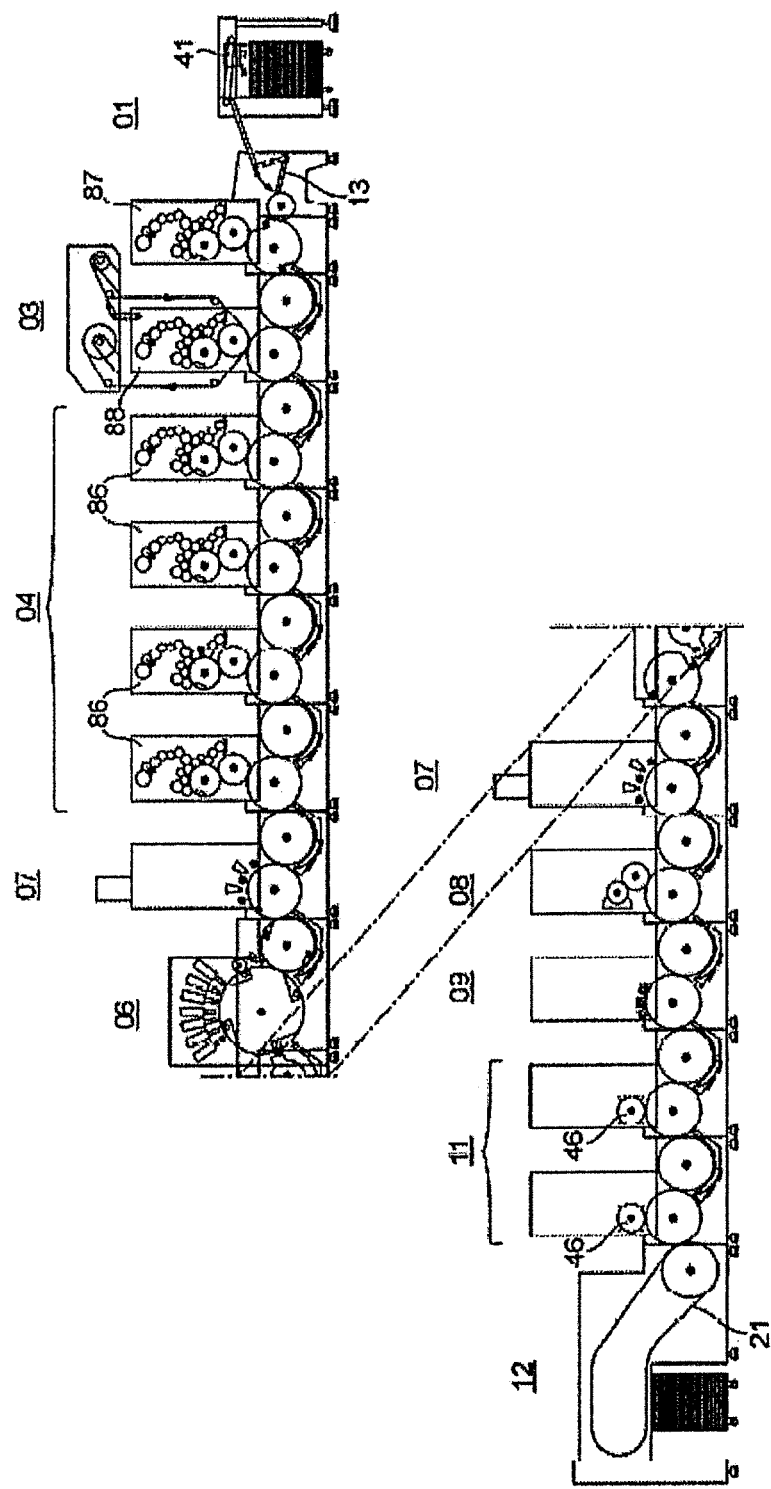

FIG. 7 shows a machine arrangement, which is shown with an offset due to its length, comprising the following processing stations 01; 02; 03; 04; 06; 07; 08; 09; 11; 12 arranged one behind the other in transport direction T of the printing stock: sheet feed unit 01; a first offset printing unit 04; cold foil application unit 03; four additional offset printing units 04 based on the unit construction principle; intermediate dryer 07; non-impact printing unit 06; intermediate dryer 07; coating unit 08; dryer 09; two mechanical further processing units 11 in the unit construction principle; delivery 12.

Figure 8:
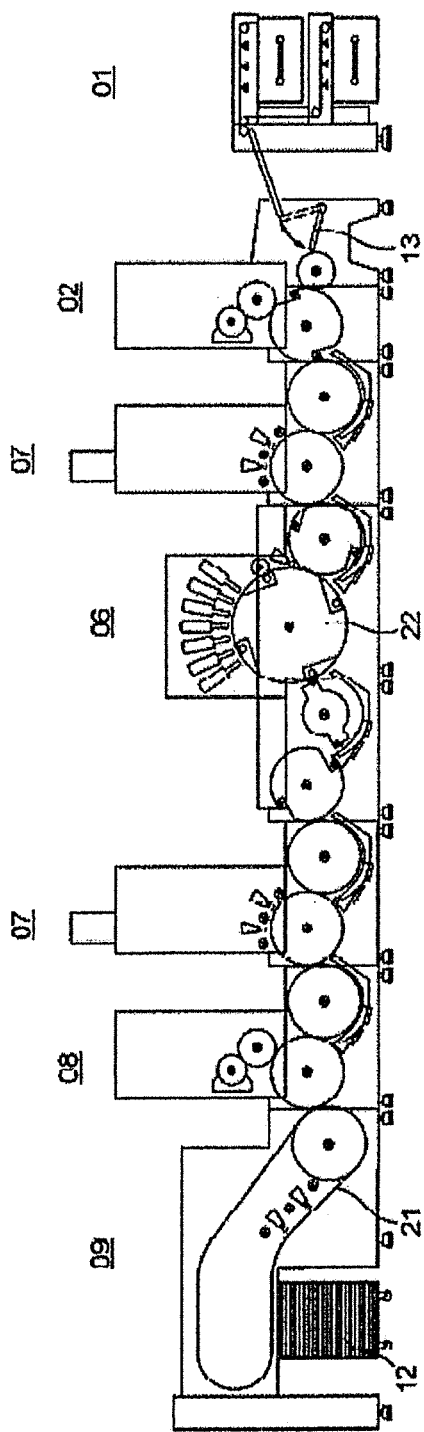

FIG. 8 shows a machine arrangement comprising the following processing stations 01; 02; 03; 04; 06; 07; 08; 09; 11; 12 arranged one behind the other in transport direction T of the printing stock: magazine feed unit 01; primer application unit 02; intermediate dryer 07; non-impact printing unit 06; intermediate dryer 07; coating unit 08; dryer 09; delivery 12.

As has already been mentioned, it is provided that with the machine arrangements described above, each comprising a plurality of processing stations 01; 02; 03; 04; 06; 07; 08; 09; 11; 12 for processing sheets and for transporting these sheets, each has at least one transport apparatus for processing sheets of different formats, i.e., of different lengths and/or widths. Thus, the sheets, which are usually rectangular, differ, e.g. in terms of their respective length, this length extending in transport direction T of the sheets in each case. When a processing station 02; 03; 04; 06; 07; 08; 09; 11; 12 embodied in particular as a non-impact printing unit 06 to which sheets are fed sequentially is used, to avoid a decrease in productivity of a machine arrangement when processing comparatively shorter sheets, i.e. sheets of a smaller format than larger-format sheets that are otherwise processed in said machine arrangement, a method having the following method steps is proposed:

A method for operating a transport apparatus for supplying a plurality of sheets sequentially to a processing station 02; 03; 04; 06; 07; 08; 09; 11; 12, wherein sheets of different lengths, said length extending in transport direction T of the sheets, are used for processing by the same processing station 02; 03; 04; 06; 07; 08; 09; 11; 12, wherein the sheets to be supplied one after another to processing station 02; 03; 04; 06; 07; 08; 09; 11; 12 are transported by the transport apparatus spaced a distance from one another, wherein the transport apparatus impresses a transport speed on each of the sheets to be transported, wherein the distance between immediately successive sheets for sheets of different lengths extending in transport direction T of these sheets is kept constant by adjusting the transport speed to be impressed upon the sheet in question by the transport apparatus, wherein the transport speed of a subsequent sheet in transport direction T is adjusted in relation to the transport speed of the sheet immediately preceding it. To achieve and/or maintain a high productivity to be rendered by processing station 02; 03; 04; 06; 07; 08; 09; 11; 12, the sheets to be supplied one after another to the relevant processing station 02; 03; 04; 06; 07; 08; 09; 11; 12 are each preferably transported by the transport apparatus at a minimal distance, but at a distance that is typically not equal to zero. The distance between successive sheets in transport direction T, i.e., between the rear edge of a preceding sheet extending transversely to transport direction T and the front edge of the immediately subsequent sheet extending transversely to transport direction T, ranges from 0.5 mm to 50 mm, for example, and is preferably less than 10 mm. If a sheet having a shorter length is to be processed after a sheet of greater length in the processing station 02; 03; 04; 06; 07; 08; 09; 11; 12 in question, the transport apparatus will accelerate the sheet having a shorter length by increasing its transport speed. Conversely, a sheet of greater length will be decelerated by the transport apparatus by decreasing its transport speed if the sheet of greater length is to be processed in the processing station 02; 03; 04; 06; 07; 08; 09; 11; 12 in question after a sheet of shorter length. A non-impact printing unit 06, the productivity of which is usually greatest when the sheets to be printed by it are supplied to it in succession at a constant minimal distance, regardless of their respective format, is preferably used as processing station 02; 03; 04; 06; 07; 08; 09; 11; 12. If a processing station 04 embodied as an offset printing unit 04, for example, is provided upstream of non-impact printing unit 06 in a machine arrangement, then regardless of their format, sheets printed in offset printing unit 04 will be supplied to the transport apparatus at a transport speed corresponding to a production speed of this offset printing unit 04, with this transport speed, which is predetermined for these sheets by offset printing unit 04, being adapted as they are transported by the transport apparatus to the transport speed that corresponds to the processing speed of non-impact printing unit 06. If these sheets will additionally be supplied to non-impact printing unit 06 at a constant distance from one another regardless of their format, then sheets of greater length are decelerated less than shorter sheets, but in any case, a reduction in their respective transport speed will be necessary because the processing speed of non-impact printing unit 06 is typically lower than the production speed of offset printing unit 04.

Each sheet is preferably held in a force-locking manner, for example by suction air and/or by grippers, during its transport by the transport apparatus. In the preferred embodiment, the transport speed to be impressed on the sheet in question is adjusted by a preferably electronic control unit, wherein the control unit performs the adjustment of the transport speed in particular to maintain a constant distance between successive sheets, for example, in a control loop. It is provided, for example, that a sheet to be supplied to mechanical further processing unit 11 is brought by rocking gripper 13 and transfer drum 31 from the second transport speed to the third transport speed, meaning that the sheet in question is accelerated in particular by the rotation of transfer drum 31 controlled by the control unit.

Figure 9:
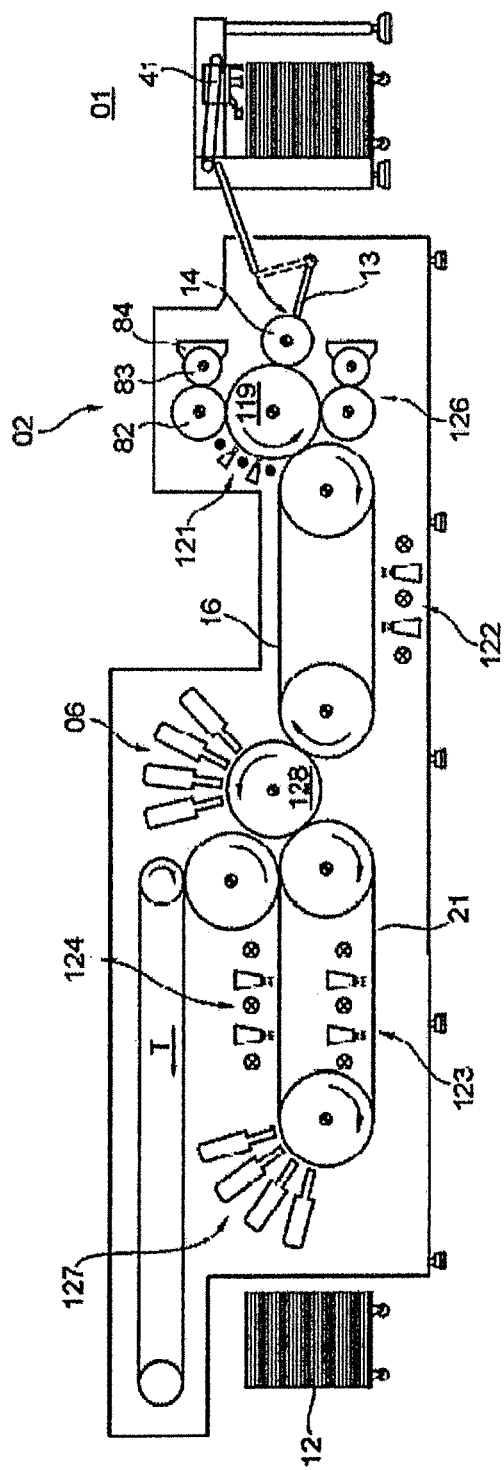
FIG. 9 shows a machine arrangement for two-sided sequential processing of a plurality of sheet-type substrates.

FIG. 9 shows another machine arrangement comprising a plurality of processing stations, typically different ones, for the sequential processing of a plurality of sheet-type substrates. The flat substrates, each having a front side and a back side, are gripped by a suction head 41, for example, in a feed unit 01 and are transferred individually by means of a rocking gripper 13 to a transfer drum 14 and from there to a rotating impression cylinder 119, wherein this impression cylinder 119 receives on its circumferential surface at least one of these substrates or a plurality thereof, for example, two or three substrates, arranged in succession in the circumferential direction. Each of the substrates to be transported is held on the circumferential surface of impression cylinder 119 by means of at least one retaining element embodied as a gripper, for example. In particular, flexible and/or thin substrates with a thickness of up to 0.1 mm, for example, or max. 0.2 mm can also be held by suction air on the circumferential surface of impression cylinder 119, for example, wherein the positioning of such a substrate against the circumferential surface of impression cylinder 119, in particular along the edges of the substrate, is supported, for example, by blower air directed in particular radially toward the circumferential surface of impression cylinder 119. Proceeding from the transfer drum 14, which is set against this impression cylinder 119, first a first primer application unit 02 for priming the front side and, following this first primer application unit 02, a second primer application unit 126 for priming the back side of the same sheet-type substrate is thrown onto impression cylinder 119 in its direction of rotation, which is indicated by a rotational direction arrow in FIG. 9, wherein the second primer application unit 126 primes the back side of the substrate in question indirectly, for example, in particular by a reverse transfer of the primer applied by this second primer application unit 126 to the circumferential surface of impression cylinder 119 and from this circumferential surface onto the back side of the substrate in question. The front side and/or back side of the substrate in question may be primed over its full surface or in partial areas as needed. Impression cylinder 119 transfers a substrate that has been primed on both sides to a first transport apparatus, for example, a transport apparatus having at least one drawing element, in particular a continuously revolving transport apparatus, to a first chain conveyor 16, for example, wherein this first transport apparatus transports this substrate to a first non-impact printing unit 06, wherein this first non-impact printing unit 06 at least partially prints the front side of the substrate in question. The first non-impact printing unit 06 transfers the substrate, which has been printed on the front side, to a second transport apparatus, for example, a transport apparatus having at least one drawing element, in particular revolving continuously, for example, to a second chain conveyor 21, wherein this second transport apparatus receives the substrate in question, in the area of its first chain wheel, for example. In the area of the second chain wheel of this second chain conveyor 21, for example, a second non-impact printing unit 127 is disposed, wherein this second non-impact printing unit 127 at least partially prints the back side of the substrate in question, which has previously been printed on the front side. Thus, first non-impact printing unit 06 and second non-impact printing unit 127 are arranged one behind the other at different positions along the transport path of the substrate in question in transport direction T of the respective sheet-type substrate. The substrate in question, now printed on both sides, is then dropped onto a pile in a delivery 12.

The machine arrangement for processing the substrate in question on both sides, illustrated in FIG. 9, has a plurality of dryers 121; 122; 123; 124, preferably four, namely a first dryer 121 for drying the primer applied to the front side of the substrate in question, and a second dryer 122 for drying the primer applied to the back side of the substrate in question. In addition, a third dryer 123 is provided for drying the substrate in question that has been printed on the front side by first non-impact printing unit 06, and a fourth dryer 124 is provided for drying the substrate in question that has been printed on the back by second non-impact printing unit 127. Dryers 121; 122; 123; 124, which are identical, for example, are embodied for drying the substrate in question, for example, by irradiation with infrared or ultraviolet radiation, with the type of radiation being dependent, in particular, upon whether the ink or printing ink applied to the substrate in question is water-based or UV curing. Transport direction T of the substrate in question transported through the machine arrangement is indicated by arrows in FIG. 9. The first non-impact printing unit 06 and the second non-impact printing unit 127 are each embodied, for example, as at least one inkjet printing unit. In the active region of first non-impact printing unit 06, a third transport apparatus is provided, which receives the substrate in question, primed on both sides, from the first transport apparatus, transports it to the second transport apparatus and delivers it to this second transport apparatus. The third transport apparatus that transports the substrate in question within the active region of first non-impact printing unit 06 is embodied as a transport cylinder 128, wherein the preferably multiple inkjet printing units of the first non-impact printing unit 06 are each arranged radially to this transport cylinder 128.

The third transport apparatus for transporting the substrate in question within the active region of the first non-impact printing unit 06 and the second transport apparatus for transporting the substrate in question within the active region of the second non-impact printing unit 127 preferably each have one dedicated drive, each of these dedicated drives being embodied as a motor that is preferably electrically driven and is adjusted or at least adjustable in terms of its rotational speed and/or angular position, wherein the printing of the substrate in question on its front side by first non-impact printing unit 06 and on its back side by second non-impact printing unit 127 is or at least can be synchronized by means of these dedicated drives that influence the respective transport apparatuses in terms of their motion behavior.

In a preferred embodiment, first dryer 121 for drying the primer that has been applied to the front side of the substrate in question is located in the region of impression cylinder 119, for example. Second dryer 122 for drying the primer that has been applied to the back side of the substrate in question is preferably located in the region of the first transport apparatus. Third dryer 123 for drying the substrate in question that has been printed on the front side by first non-impact printing unit 06 is located in the region of the second transport apparatus or is situated in the region of the third transport apparatus, which is in turn situated in the active region of first non-impact printing unit 06 and cooperates with it. Fourth dryer 124 for drying the substrate in question that has been printed on the back by second non-impact printing unit 127 is located downstream of the third transport apparatus in transport direction T of the substrate in question that is transported through the machine arrangement, for example.

The machine arrangement illustrated in FIG. 9 can also be described as a machine arrangement for the sequential processing of a plurality of sheet-type substrates each having a front side and a back side, wherein a first non-impact printing unit 06 and a second non-impact printing unit 127 as well as a first primer application unit 02 and a second primer application unit 126 are provided, wherein in each case with respect to the same sheet-type substrate, first primer application unit 02 is situated for priming the front side and second primer application unit 126 is situated for priming the back side, and wherein with respect to this substrate, first non-impact printing unit 06 is situated for printing the front side that has been primed by first primer application unit 02, and second non-impact printing unit 127 is situated for printing the back side that has been primed by the second primer application unit 126. A first dryer 121 for drying the primer that has been applied to the front side of the substrate in question is provided upstream of first non-impact printing unit 06 in transport direction T of the substrate in question, and a second dryer 122 for drying the primer that has been applied to the back side of the substrate in question is arranged upstream of second non-impact printing unit 127 in transport direction T of the substrate in question, and a third dryer 123 for drying the substrate in question that has been printed on the front side by first non-impact printing unit 06 is provided downstream of first non-impact printing unit 06 in transport direction T of the substrate in question, and a fourth dryer 124 for drying the substrate in question that has been printed on the back side by second non-impact printing unit 127 is provided downstream of second non-impact printing unit 127 in transport direction T of the substrate in question. The second primer application unit 126 may optionally be located upstream or downstream of second non-impact printing unit 127 in transport direction T of the substrate in question. First dryer 121 for drying the primer applied to the front side of the substrate in question, and/or second dryer 122 for drying the primer applied to the back side of the substrate in question, and/or third dryer 123 for drying the substrate in question that has been printed by first non-impact printing unit 06 and/or fourth dryer 124 for drying the substrate in question that has been printed on the back side by second non-impact printing unit 127 are each embodied, for example, as a dryer that dries the primed and/or printed substrate in question using hot air and/or by irradiation with infrared or ultraviolet radiation, wherein dryer 121; 122; 123; 124 that dries the primed and/or printed substrate in question by irradiation with infrared or ultraviolet radiation is preferably embodied as an LED dryer, i.e., as a dryer that uses semiconductor diodes. In addition, at least one transport apparatus for transporting the substrate in question is provided, wherein this transport apparatus is embodied as a transport cylinder or as a revolving transport belt or as a chain conveyor. The at least one transport apparatus for transporting the substrate in question has at least one retaining element, wherein the at least one retaining element is embodied to hold the substrate in question in a force-locking or a form-fitting manner.

Figure 10:
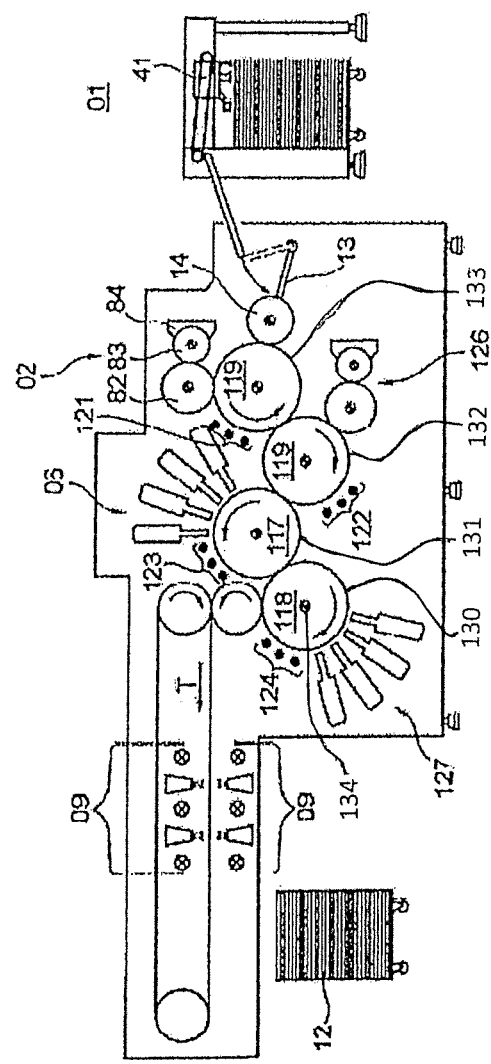
FIG. 10 shows another machine arrangement without a turning device for two-sided sequential processing of a plurality of sheet-type substrates.

FIG. 10 shows yet another advantageous machine arrangement for the sequential processing of a plurality of sheet-type substrates each having a front side and a back side. This machine arrangement, preferably embodied as a printing machine, in particular as a sheet-fed printing machine, comprises at least one first printing cylinder 117 and one second printing cylinder 118. At least one first non-impact printing unit 06 for printing on the front side of the substrate in question, and, downstream of the first non-impact printing unit 06 in the direction of rotation of the first printing cylinder 117, a dryer 123 that dries the front side of the substrate in question that has been printed by first non-impact printing unit 06 are provided, each on the periphery of the first printing cylinder 117, and at least one second non-impact printing unit 127 for printing on the back side of the substrate in question, and, downstream of the second non-impact printing unit 127 in the direction of rotation of the second printing cylinder 118, a dryer 124 for drying the back side of the substrate in question that has been printed by the second non-impact printing unit 127 are provided, each on the periphery of the second printing cylinder 118. First non-impact printing unit 06 and second non-impact printing unit 127 are each embodied, e.g. as at least one inkjet printing unit. First non-impact printing unit 06 and/or second non-impact printing unit 127 each print in a plurality of printing inks, for example, four printing inks, in particular the printing inks yellow, magenta, cyan and black, wherein a specific inkjet printing unit is preferably provided for each of these printing inks in each of the non-impact printing units 06; 127 in question.

In the machine arrangement according to FIG. 10, first printing cylinder 117 and second printing cylinder 118 are arranged such that they form a common roller nip, wherein in this common roller nip, first printing cylinder 117 transfers the substrate in question, which has been printed on the front side and dried, directly to second printing cylinder 118. In the preferred embodiment of this machine arrangement, a first primer application unit 02 and a second primer application unit 126 are also provided, wherein the first primer application unit 02 is arranged to prime the front side and the second primer application unit 126 is arranged to prime the back side of the same sheet-type substrate in each case, wherein with respect to this substrate, first non-impact printing unit 06 is arranged to print the front side that has been primed by first primer application unit 02, and second non-impact printing unit 127 is arranged to print the back side that has been primed by second primer application unit 126. First primer application unit 02 and second primer application unit 126 each comprise an impression cylinder 119, for example, wherein these two impression cylinders 119 are arranged to form a common roller nip, wherein in this common roller nip, the impression cylinder 119 that has the first primer application unit 02 transfers the substrate in question directly to the impression cylinder 119 that has the second primer application unit 126. The impression cylinder 119 that has the second primer application unit 126 and the first printing cylinder 117 that has the first non-impact printing unit 06 are arranged to form a common roller nip, wherein the impression cylinder 119 that has the second primer application unit 126 transfers the substrate in question directly to the first printing cylinder 117 that has the first non-impact printing unit 06.

A dryer 121 for drying the front side of the substrate in question that has been primed by the first primer application unit 02 is disposed on the periphery of the impression cylinder 119 that has this first primer application unit 02, typically directly downstream of the first primer application unit 02, for example, and/or a dryer 122 for drying the back side of the substrate in question that has been primed by the second primer application unit 126 is arranged on the periphery of the impression cylinder 119 that has this second primer application unit 126, typically immediately downstream of the second primer application unit 126. Dryer 121 for drying the primer applied to the front side of the substrate in question, and/or dryer 122 for drying the primer applied to the back side of the substrate in question, and/or dryer 123 for drying the substrate in question that has been printed on the front side by first non-impact printing unit 06, and/or dryer 124 for drying the substrate in question that has been printed on the back side by second non-impact printing unit 127 is/are each embodied as a dryer that dries the primed and/or printed substrate in question using hot air and/or by irradiation with infrared or ultraviolet radiation. In a particularly preferred embodiment, dryer 121; 122; 123; 124 that dries the primed and/or printed substrate in question by irradiation with infrared or ultraviolet radiation is embodied as an LED dryer, i.e., as a dryer that generates infrared or ultraviolet radiation by means of semiconductor diodes.

Moreover, in the machine arrangement according to FIG. 10, first printing cylinder 117 and second printing cylinder 118 and the impression cylinder 119 that has first primer application unit 02 and the impression cylinder 119 that has second primer application unit 126 are each connected to one another, preferably in a single drive train formed from gear wheels, i.e., in a gear train, and are driven jointly in their respective rotation by a single drive, wherein this drive is preferably embodied as an electric motor, in particular as a speed-controlled and/or position-controlled electric motor. First printing cylinder 117 and second printing cylinder 118 and the impression cylinder 119 that has first primer application unit 02 and the impression cylinder 119 that has second primer application unit 126 are each embodied as multiple-sized, for example, i.e., a plurality of substrates, e.g. two or three or four, is or at least can be arranged one behind the other in the circumferential direction on their circumferential surface. Each one of the substrates to be transported is retained in a force-locking and/or form-fitting manner on the circumferential surface of first printing cylinder 117 and/or of second printing cylinder 118 and/or of the impression cylinder 119 that has first primer application unit 02 and/or of the impression cylinder 119 that has second primer application unit 126, the retention being by means of at least one retaining element embodied as grippers, for example. In particular, flexible and/or thin substrates having a thickness of up to 0.1 mm, for example, or max. 0.2 mm may be held in a force-locking manner, for example, by means of suction air on the circumferential surface of the cylinder 117; 118; 119 in question, wherein the positioning of such a substrate against the circumferential surface of the cylinder 117; 118; 119 in question, in particular along the edges of this substrate, is supported, for example, by blower air directed in particular radially toward the circumferential surface of the cylinder 117; 118; 119 in question.

The substrate in question that has been printed on both sides is then preferably transported, following its transport through second printing cylinder 118, by means of a transport apparatus to a delivery 12, for example, and is deposited onto a pile in delivery 12. The transport apparatus connected to second printing cylinder 118 is embodied, for example, as a chain conveyor, wherein the substrate in question is preferably dried again on both sides by means of at least one dryer 09 during its transport by this transport apparatus and before being deposited in delivery 12. In some production lines, the intention may be for the substrate in question that has already been printed on the front side by first non-impact printing unit 06 and/or on the back side by second non-impact printing unit 127 to be printed on one or both sides with additional printing inks, in particular special inks, and/or surface finished by a coating application, for example. In this latter case, following second printing cylinder 118, upstream of the transport apparatus for transporting the substrate in question to delivery 12, at least one additional printing cylinder is provided, for example a third printing cylinder, or preferably at least one additional cylinder pair formed by a third printing cylinder and a fourth printing cylinder, on which at least one additional printing cylinder, for example a third and/or a fourth printing cylinder, is arranged in the same manner as on first printing cylinder 117 and/or on second printing cylinder 118, each in turn forming an additional printing unit, in particular an additional non-impact printing unit, or at least one coating unit 08, each optionally having an additional dryer. All of these printing cylinders aligned in a row then form a continuous transport path for the substrate in question in the machine arrangement in question, in which this substrate is then transferred from one printing cylinder to the next. The substrate in question can be processed, in particular printed, on both sides, without requiring a turning unit 23 for this substrate in this machine arrangement. The proposed machine arrangement is thus very compact and inexpensively constructed. The machine arrangement illustrated in FIG. 10 is particularly advantageous in combination with UV curing inks, for example, in printing packaging for food items or cosmetics.

Figure 11:
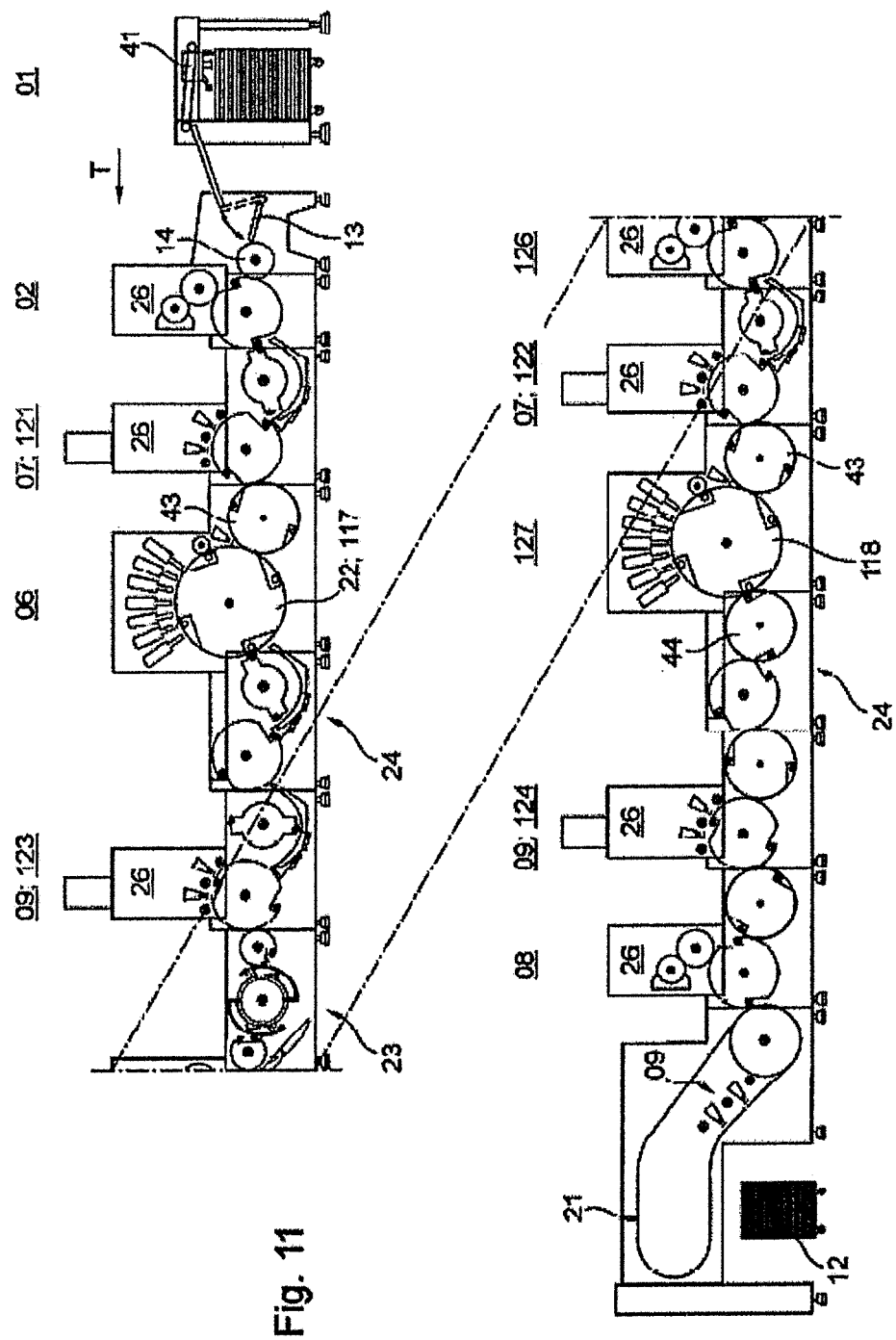
FIG. 11 shows yet another machine arrangement having a turning device for two-sided sequential processing of a plurality of sheet-type substrates.

FIG. 11 shows as an example a machine arrangement comprising a plurality of processing stations 01; 02; 03; 04; 06; 07; 08; 09; 11; 12, the processing stations 01; 02; 03; 04; 06; 07; 08; 09; 11; 12 being arranged one behind the other in transport direction T of the substrates. Each of the processing stations 01; 02; 03; 04; 06; 07; 08; 09; 11; 12 is embodied as an independently functional module, with each of the modules forming a machine unit installed in its own frame. In the preferred embodiment, the modules that are embodied as a coating unit 02; 03; 08 (i.e., primer application unit 02; 126, cold foil application unit 03 and coating unit 08) or as a dryer 07; 09; 121; 122; 123; 124 or as a printing unit 04; 06; 127 or as a mechanical further processing unit 11 each has a substrate guide unit 24 and a substrate processing unit 26. The substrate guide unit 24 has a transport cylinder assembly 17; 19 for transporting the substrates, for example, or one or more transport cylinders 128 or one or more transfer drums 43; 44. Substrate processing unit 26 comprises the actual coating unit 02; 03; 08 or dryer 07; 09; 121; 122; 123; 124 or at least one printing forme 86; 87; 88 of printing unit 04; 06; 127 or at least one processing unit 46 of mechanical further processing unit 11, depending on the type of processing station 01; 02; 03; 04; 06; 07; 08; 09; 11; 12 in each case.

The machine arrangement illustrated in FIG. 11 is a machine arrangement for perfecting printing and, starting from a feed unit 01 embodied as a sheet feed unit 01 or a magazine feed unit 01 that grips stacked substrates one after another with a suction head 41, for example, and from a downstream rocking gripper 13 with a transfer drum 14, comprises a coating unit 02; 03; 08, in particular in the form of a first primer application unit 02, followed by a first dryer 07; 121, one behind the other in transport direction T of the substrates (sheets). The substrates pretreated on the front side in this way are then each sent to a first non-impact printing unit 06 for printing the front side of the substrates with a first printing cylinder 22; 117, wherein this first printing cylinder 22; 117 is preferably embodied as triple-sized or quadruple-sized, which means that this first printing cylinder 22; 117 has at least enough retaining elements on its periphery that three or four substrates are or at least can be arranged such they are held in a force-locking manner and/or in a form-fitting manner one behind the other on its periphery. As a rule, at least one retaining element is assigned to each substrate to be held on the periphery of printing cylinder 22; 117, wherein retaining elements that are assigned to different substrates can each be operated separately, i.e., independently of one another. Retaining elements embodied as grippers are disposed in a channel, in particular, each channel extending axially on the circumferential surface of the printing cylinder 22; 117 in question. This means that, for example, if four substrates can be arranged along the periphery of printing cylinder 22; 117, the printing cylinder 22; 117 in question will have four channels, with at least one retaining element being disposed in each channel. It is also possible for at least two retaining elements to be arranged in a channel, wherein one of these retaining elements holds an edge of a first one of these substrates, said edge being at the rear in transport direction T of the substrates, and another one of these retaining elements holds a front edge of a second substrate directly following the first substrate on the periphery of the printing cylinder 22; 117 in question, said edge being at the front in transport direction T of the substrates. Preferably, a plurality of inkjet printing units is arranged one behind the other along a part of the periphery of first printing cylinder 22; 117. In the preferred embodiment, a substrate guide unit 24 embodied as a simple transport module without an additional substrate processing unit 26 follows the first non-impact printing unit 06. This transport module is also mounted in a separate frame. In this machine arrangement, this substrate guide unit 24 allows the formation of a sufficiently wide transverse gallery which in turn improves accessibility to first non-impact printing unit 06, for example, for maintenance and/or repair work. Downstream of substrate guide unit 24, a second dryer 09; 123 for drying the printed front side of the substrates is provided. Second dryer 09; 123 is followed by a turning device 23, which makes it possible for the back side of the substrates to be printed subsequently. As described previously for front side printing, i.e., for printing the front side, the substrates coming from turning device 23 are sent first to a second primer application unit 126 which treats the back side of the substrates, and then to a third dryer 07; 122. This is followed by a second non-impact printing unit 127, which prints the back side of the substrates with a second printing cylinder 118, wherein this second printing cylinder 118 is again preferably embodied as triple-sized or quadruple-sized, which means that this second printing cylinder 118 has on its periphery enough retaining elements that three or four substrates are or at least can be arranged one behind the other and held in a force-locking and/or form-fitting manner. Along part of the periphery of second printing cylinder 118, a plurality of inkjet printing units is preferably arranged one behind the other. For the same reason as has already been explained, a substrate guide unit 24 is preferably also located downstream of second non-impact printing unit 127 without an additional substrate processing unit 26. This is followed by a fourth dryer 09; 124 for drying the printed back side of the substrates. In the preferred embodiment, this is followed by a coating unit 08. The coated substrates are then dried in an additional dryer 09, wherein this dryer 09 is arranged, for example, in the transport path of a transport apparatus embodied as a chain conveyor 21, wherein this transport apparatus transports the substrates to a delivery 12, in particular to a multi-pile delivery, and are delivered there. In the machine arrangement of FIG. 11 the substrate guide units 24, each having a transport cylinder assembly 17; 19, apart from the two printing cylinders 22; 117; 118, are preferably each embodied as double-sized, so that two substrates are or at least can be arranged one behind another on the periphery of the transport cylinder 128 or the transfer drums 43; 44.

Figure 12:
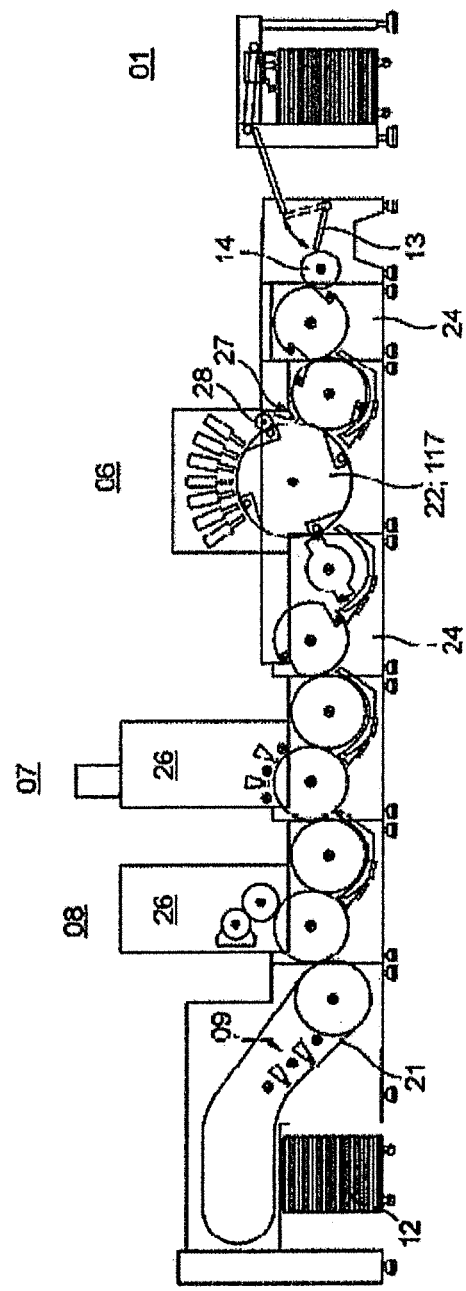
FIG. 12 shows a machine arrangement having substrate guide elements of different lengths.

FIG. 12 shows as an example a machine arrangement for one-sided processing of substrates, in particular for the one-sided printing thereof. The substrates coming from a feed unit 01 are transferred by means of a rocking gripper 13 to a transfer drum 14 and from there are fed via a substrate guide unit 24 having, for example, only a single transport cylinder 128 or only a single transfer drum 43; 44 to a non-impact printing unit 06 having a triple-sized or quadruple-sized printing cylinder 22; 117, which prints the front side of each of the substrates. To improve the positioning of the substrates against the circumferential surface of printing cylinder 22; 117, for example, a blower air device 27 and/or a pressing element 28, for example, in the form of a smoothing roller are provided. This is followed by a substrate guide unit 24 with a transport cylinder assembly 17; 19 having at least two transport cylinders 128 or transfer drums 43; 44. These are then followed by a dryer 07 and a coating unit 08. The coated substrates are then dried in an additional dryer 09, wherein this dryer 09 is again arranged, for example, in the transport path of a transport apparatus embodied as a chain conveyor 21, wherein this transport apparatus transports the substrates to a delivery 12 and delivers them there. Substrate guide units 24, apart from printing cylinders 22; 117, preferably have transport cylinders 128 or transfer drums 43; 44 that are each embodied as double-sized. A substrate guide unit 24 with a transport cylinder assembly 17; 19 having at least two transport cylinders 128 or transfer drums 43; 44 extends in transport direction T of the substrates over a length corresponding to at least one-and-a-half times the diameter of the transport cylinder 128 or transfer drum 43; 44 in question.

Figure 13:
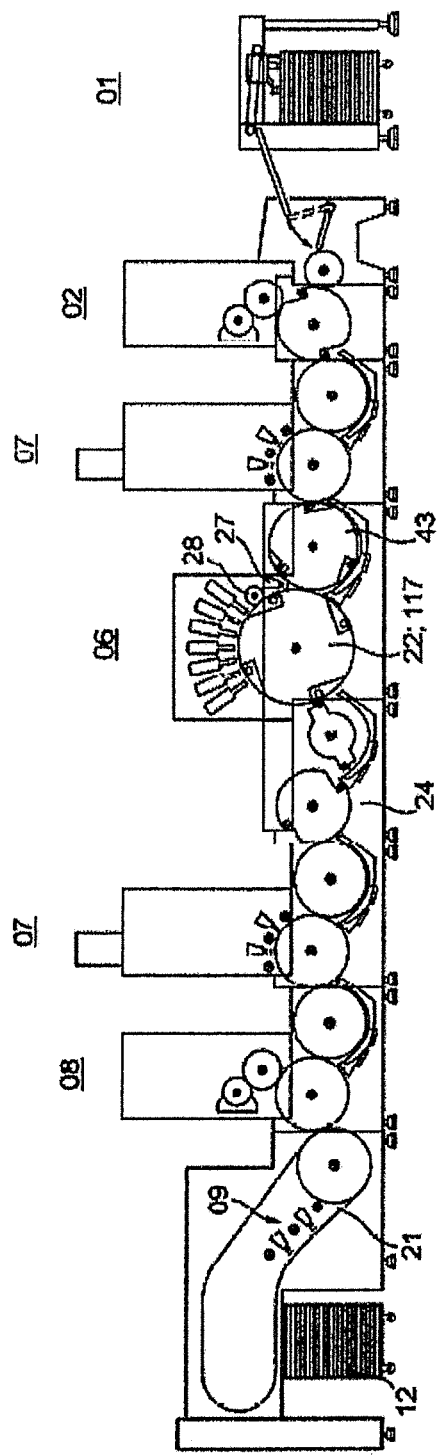
FIGS. 13 to 15 show machine arrangements having a printing cylinder and a transfer drum in various formats.
Figure 14:
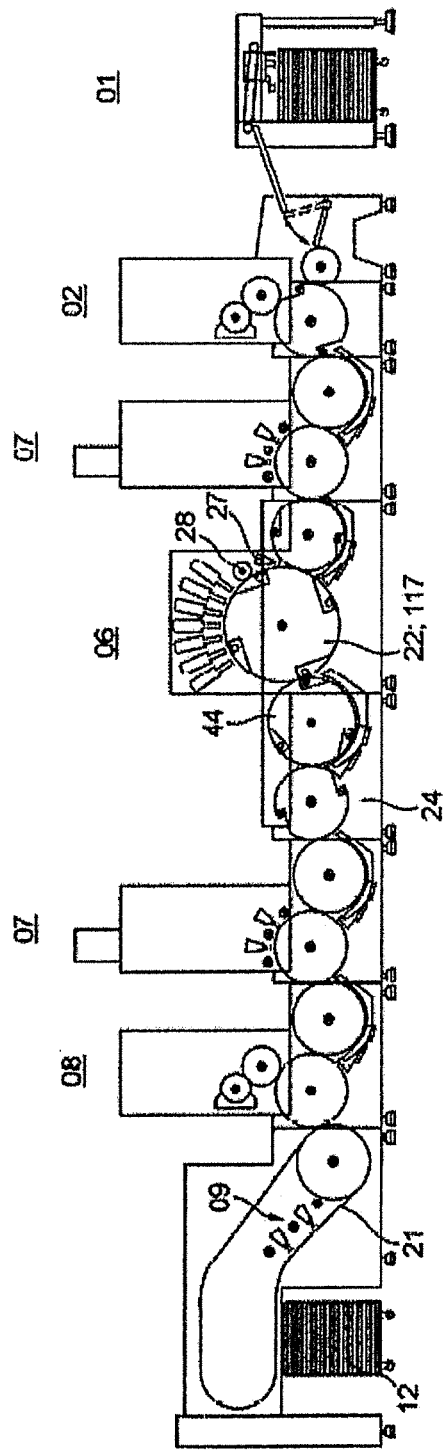
Figure 15:
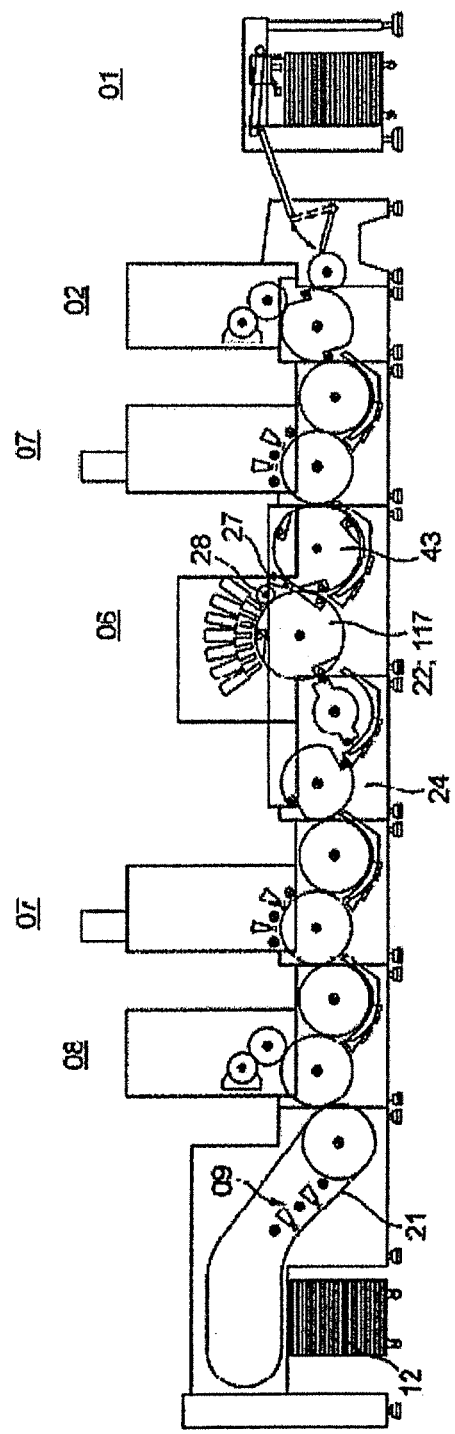

FIGS. 13 to 15 each show as an example a machine arrangement for the one-sided processing of substrates, in particular for the one-sided printing thereof, wherein a primer application unit 02 and a dryer 07 are provided downstream of feed unit 01. These are followed in the machine arrangement by a non-impact printing unit 06, a substrate guide unit 24, another dryer 07, a coating unit 08 and a dryer 09 arranged, for example, in the transport path of a transport apparatus embodied as a chain conveyor 21, wherein this transport apparatus transports the substrates to a delivery 12 and delivers them there.

In the machine arrangement of FIG. 13, printing cylinder 22; 117 is embodied as quadruple-sized. The quadruple-sized printing cylinder 22; 117 receives the substrates to be printed from a transfer drum 43 immediately upstream, which is embodied as triple-sized. In the machine arrangement of FIG. 14, printing cylinder 22; 117 is likewise embodied as quadruple-sized, however quadruple-sized printing cylinder 22; 117 transfers the printed substrates to a transfer drum 44 directly downstream of this printing cylinder 22; 117 and embodied as triple-sized. FIG. 14 shows the quadruple-sized embodiment of printing cylinder 22; 117, with a double-sized embodiment of transfer drum 43 directly upstream of this printing cylinder 22; 117. The circumferential surface of printing cylinder 22; 117 and transfer drum 43 are preferably arranged in physical contact with one another due to the formation of a common roller strip 32. In the machine arrangement of FIG. 15, printing cylinder 22; 117 and the transfer drum 43 immediately upstream of this printing cylinder 22; 117 are each embodied as triple-sized. The machine arrangements of FIGS. 13 to 15 each differ in terms of the format of printing cylinder 22; 117 and a transfer drum 43; 44 immediately upstream or downstream of this printing cylinder 22; 117. A printing cylinder 22; 117 embodied as quadruple-sized has a diameter of approx. 1200 mm, for example. A transfer drum 43 embodied as double-sized has a diameter of approx. 600 mm, for example. The format of printing cylinder 22; 117 and the format of a transfer drum 43; 44 immediately upstream or downstream of this printing cylinder 22; 117 are determined by the number of retaining elements arranged on the respective circumference of each, wherein the retaining elements hold each of the substrates in a force-locking and/or a form-fitting manner on the periphery of the printing cylinder 22; 117 or the transfer drum 43; 44 in question. A plurality of inkjet printing units and, e.g. a blower air device 27 and/or a pressing element 28, e.g. in the form of a smoothing roller, are arranged on the periphery of each printing cylinder 22; 117 in question.

While preferred embodiments of a machine arrangement and method for sequential processing of sheet-type substrates, in accordance with the present invention, have been set forth fully and completely hereinabove, it will be apparent to one of skill in the art that various changes could be made without departing from the true spirit and scope of the invention which is accordingly to be limited only by the appended claims.

The invention claimed is:

1. A machine arrangement for the sequential processing of sheet-type substrates, comprising a plurality of processing stations, wherein a first one of the plurality of the processing stations includes a non-impact printing unit for printing each of the sheet-type substrates, wherein a primer application unit for priming each of the sheet-type substrates and a first dryer for drying the primer applied to each of the sheet-type substrates are provided as additional ones of the plurality of processing stations, wherein the primer application unit and the first dryer are each arranged upstream of the non-impact printing unit in a transport direction of the sheet-type substrates, wherein the first one of the plurality of processing stations that comprises the non-impact printing unit includes a printing cylinder, wherein the non-impact printing unit for printing each of the sheet-type substrates is located on the periphery of the printing cylinder, wherein, downstream of the first one of the plurality of processing stations that comprises the non-impact printing unit for printing the substrates, in the transport direction of the sheet-type substrates, a second one of the plurality of processing stations is provided, and having a second dryer for drying the sheet-type substrates that have been printed by the non-impact printing unit, wherein downstream of the second one of the plurality of processing stations that comprises the second dryer for drying the printed sheet-type substrates, in the transport direction of the sheet-type substrates, a third one of the plurality of processing stations, and having a coating unit is provided, and downstream of the coating unit, a fourth one of the plurality of processing stations having a third dryer is provided, wherein the printing cylinder is embodied as one of triple-size and quadruple-sized, whereby one of three and four of the sheet-type substrates one of are and can be arranged, one behind the other, in a circumferential direction, on a circumferential surface of the printing cylinder, wherein each of the sheet-type substrates to be transported is held on the circumferential surface of the printing cylinder, in one of a force-locking manner by suction air and in a form-fitting manner by at least one gripper, and wherein the one of the primer and the coating material are applied to at least pre-selected areas of the surface of each of the sheet-type substrates, which pre-selected areas are less than an entire surface of the each of the sheet-type substrates.

2. The machine arrangement according to claim 1, wherein at least one of the first dryer for drying the primer that is applied to the sheet-type substrates, and the second dryer for drying the sheet-type substrates printed by the non-impact printing unit, and the third additional dryer is embodied as a dryer for drying each of the one of the primed and printed and coated sheet-type substrates using one of hot air and by irradiation with one of infrared and ultraviolet radiation.

3. The machine arrangement according to claim 2, wherein the at least one of the first, second and third dryers for drying each of the sheet-type substrates by irradiation with one infrared and ultraviolet radiation is embodied as an LED dryer.

4. The machine arrangement according to claim 1, wherein the non-impact printing unit for printing the sheet-type substrates comprises one of four and five and six and seven inkjet printing units, each inkjet printing unit being controlled individually, and wherein these inkjet printing units are arranged one behind the other in the transport direction of the sheet-type substrates.

5. The machine arrangement according to claim 1, wherein the non-impact printing unit for printing the sheet-type substrates is configured such that it is able to print each of the sheet-type substrates at least nearly over an entire width of each of the sheet-type substrates, oriented transversely to the transport direction.

6. The machine arrangement according to claim 1, wherein the one of the plurality of processing stations that comprises the primer application unit includes a printing couple cylinder, which printing couple cylinder cooperates with an impression cylinder and has a forme roller in the form of an anilox roller, which anilox roller one of is and can be thrown onto the printing couple cylinder, and which anilox roller also includes one of at least one doctor blade that extends in an axial direction of the forme roller and an ink chamber blade system.

7. The machine arrangement according to claim 1, wherein at least those ones of the plurality of processing stations that comprise one of the non-impact printing unit and the primer application unit and the first dryer situated downstream of the primer application unit and each one of the plurality of processing stations are each arranged in their own frame as one of a separately installed machine unit and a functional subassembly.

8. The machine arrangement according to claim 1, wherein a transport module, formed as a sheet-type substrate guide unit, with no sheet-type substrate processing unit, is situated one of immediately upstream and downstream of the first one of the plurality of processing stations that includes the printing cylinder assigned to the non-impact printing unit for printing the sheet-type substrates.

9. The machine arrangement according to claim 1, wherein the ones of the plurality of processing stations that comprise one of the printing unit and one of the first, second and third dryers and the coating unit each include a transport apparatus having a plurality of transport units arranged one behind the other in the transport direction of the sheet-type substrates and with each transport unit having at least one transport cylinder.

10. The machine arrangement according to claim 1, wherein one of the primer application unit is configured to apply the primer to the sheet-type substrates over the entire surface of the sheet-type substrates and the coating unit is configured to apply the coating to the sheet-type substrates over the entire surface area of the sheet-type substrates.

11. The machine arrangement according to claim 1, wherein the sheet-type substrates are each made of one of a paper and of a single-layer paperboard and of a multi-layer paperboard and of a cardboard.

12. The machine arrangement according to claim 1, wherein the machine arrangement is configured for processing each of the sheet-type substrates to produce packaging means.

\* \* \* \* \*